US008431527B2

(12) United States Patent
Brown et al.

(10) Patent No.: US 8,431,527 B2
(45) Date of Patent: *Apr. 30, 2013

(54) METHODS FOR ALLEVIATING DELETERIOUS EFFECTS OF 3-DEOXYGLUCOSONE

(75) Inventors: Truman R. Brown, Cornwall-on-Hudson, NY (US); Francis Kappler, Phila, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/911,195

(22) Filed: Oct. 25, 2010

(65) Prior Publication Data

US 2011/0034522 A1 Feb. 10, 2011

Related U.S. Application Data

(63) Continuation of application No. 11/834,314, filed on Aug. 6, 2007, now abandoned, which is a continuation of application No. 11/478,497, filed on Jun. 29, 2006, now abandoned, which is a continuation of application No. 09/974,323, filed on Oct. 10, 2001, now Pat. No. 7,071,298, which is a continuation-in-part of application No. 09/182,114, filed on Oct. 28, 1998, now abandoned, which is a continuation-in-part of application No. 09/095,953, filed on Jun. 11, 1998, now abandoned, which is a continuation-in-part of application No. PCT/US98/02192, filed on Feb. 5, 1998, which is a continuation-in-part of application No. 08/794,433, filed on Feb. 5, 1997, now Pat. No. 6,004,958.

(51) Int. Cl.
  *A61K 38/00* (2006.01)
(52) U.S. Cl.
  USPC .......................................... 514/2.1; 530/322
(58) Field of Classification Search ................ None
  See application file for complete search history.

(56) References Cited

U.S. PATENT DOCUMENTS

| | | | |
|---|---|---|---|
| 4,371,374 A | 2/1983 | Cerami et al. | |
| 4,708,868 A * | 11/1987 | Brickl et al. | .................. 514/309 |
| 4,748,174 A | 5/1988 | Veronesi | |
| 4,761,368 A | 8/1988 | Cerami | |
| 4,798,583 A | 1/1989 | Beck et al. | |
| 4,837,170 A | 6/1989 | Ohe et al. | |
| 4,910,208 A * | 3/1990 | Misra | ............................. 514/311 |
| 5,028,625 A | 7/1991 | Motola et al. | |
| 5,108,930 A | 4/1992 | Ulrich et al. | |
| 5,114,943 A | 5/1992 | Ulrich et al. | |
| 5,128,360 A | 7/1992 | Cerami et al. | |
| 5,130,324 A | 7/1992 | Ulrich et al. | |
| 5,130,337 A | 7/1992 | Ulrich et al. | |
| 5,192,753 A | 3/1993 | McGeer et al. | |
| 5,221,683 A | 6/1993 | Ulrich et al. | |
| 5,231,031 A | 7/1993 | Szwergold et al. | |
| 5,243,071 A | 9/1993 | Ulrich et al. | |
| 5,258,381 A | 11/1993 | Ulrich et al. | |
| 5,262,152 A | 11/1993 | Ulrich et al. | |
| 5,272,165 A | 12/1993 | Ulrich et al. | |
| 5,318,982 A | 6/1994 | Ulrich et al. | |
| 5,334,617 A | 8/1994 | Ulrich et al. | |
| 5,358,960 A | 10/1994 | Ulrich et al. | |
| 5,468,777 A | 11/1995 | France et al. | |
| 5,476,849 A | 12/1995 | Ulrich et al. | |
| 5,877,217 A | 3/1999 | Ulrich et al. | |
| 5,891,341 A | 4/1999 | Li | |
| 5,892,000 A | 4/1999 | Founds | |
| 5,935,927 A | 8/1999 | Vitek | |
| 5,955,481 A | 9/1999 | Ohara | |
| 6,004,958 A * | 12/1999 | Brown et al. | ............... 514/238.8 |
| 7,071,298 B2 | 7/2006 | Brown et al. | |
| 7,615,528 B2 * | 11/2009 | Brown et al. | ................... 514/1.1 |

FOREIGN PATENT DOCUMENTS

| | | |
|---|---|---|
| JP | 7033667 | 2/1995 |
| WO | 97/09981 | 3/1997 |
| WO | 98/43649 | 10/1998 |
| WO | 99/25690 | 5/1999 |

OTHER PUBLICATIONS

Dyer et al., J. Clin. Invest., 1993, vol. 91, p. 2463-9.*
Ahmed et al., J. Biol. Chem., 1986, vol. 261, p. 4889-94.*
Dunn et al., Biochem., 1989, vol. 28, p. 9464-8.*
Scalbert et al., Exp. Eye Res. , 1993, vol. 56, p. 335-40.*
Fu et al., J. Biol. Chem., 1996, vol. 271, p. 9982-6.*
Zyzak et al., Archives of Biochem. and Biophys., 1995, vol. 316, p. 547-54.*

(Continued)

*Primary Examiner* — Cecilia J Tsang
*Assistant Examiner* — Li Lee
(74) *Attorney, Agent, or Firm* — Patrick J. Hagan; Dann, Dorfman, Herrell and Skillman, PC

(57) ABSTRACT

Disclosed is a class of compounds which inhibit the enzymatic conversion of fructose-lysine into fructose-lysine-3-phosphate in an ATP dependent reaction in a newly discovered metabolic pathway. According to the normal functioning on this pathway, fructose-lysine-3-phosphate (FL3P) is broken down to form free lysine, inorganic phosphate and 3-deoxyglucosone (3DG), the latter being a reactive protein modifying agent. 3DG can be detoxified by reduction to 3-deoxyfructose (3DF), or it can react with endogenous proteins to form advanced glycation end-product modified proteins (AGE-proteins) Also disclosed are therapeutic methods of using such inhibitors to alleviate deleterious effects of 3DG.

7 Claims, 6 Drawing Sheets

OTHER PUBLICATIONS

Nagaraj and Sady, FEBS Letters, 1996, vol. 382, p. 234-8.*
Su et al., "Identification of Tagatoselysine 3-Phosphate in Hyperglycemic Kidneys", Abstracts presented at the Amer. Society of Nephrology Conference, Oct. 26-29, 1994.
Szwergold et al., "Identification of a Novel Phosphononester from Mammalian Kidneys as a Secondary Phosphate Ester of Fructosyl-Lysine", Abstract presented at the Int'l Soc. of Magnetic Resonance, Aug. 14-20, 1993.
Kappler et al., "Metabolism of Fructoselysine in the Kidney", Abstract presented at the American Society of Nephrology Meeting, Nov. 3-6, 1996.
Lal et al., Metabolism of Fructose 3-phosphate in the Diabetic Rat Lens, Archives of Biochem. Biophys., 318: 191-199 (1995).
Szwergold et al., "Identification of Fructose 3-Phosphate in the Lens of Diabetic Rats", Science, 247: 451-454 (1990).
Lal et al., "Production of Fructose and Fructose-3-phosphate in Maturing Rat Lenses", Investigative Ophthalmology & Visual Science, 36: 969-973 (1995).
Szwergold et al., "31P-Nuclear Magnetic Resonance Evidence of an Activated Hexose-Monophosphate Shunt in Hyperglycemic Rat Lenses in Vivo", Diabetes, 14: 810-815 (1995).
Kappler et al., "Identification of Galactitol 2-Phosphate and Galactitol 3-Phosphate in the Lens of galactose-Fed Rats", Metabolism, 44: 1527-1531 (1995).
Tooke et al., "Perspectives in Diabetes Microvascular Function in Human Diabetes A Physiological Perspective", Diabetes, 4: 721-725 (1995).
Monnier et al., "Accelerated age-related browning of human collagen in diabetes mellitus", Proc. Natl. Acad. Sci. USA, 81: 583-587 (1984).
Lee et al., "Glycosylation of Lens Proteins in Senile Cataract and Diabetes Mellitus", Biochem. Biophys. Res. Comm., 123: 888-893 (1984).
Engerman et al., "Progression of Incipient Diabetic Retinopathy During Good Glycemic Control", Diabetes, 36: 808-812 (1987).
Harrington et al., "A glycation connection", Nature 370: 247-248 (1994).
Knecht et al., "Detection of 3-Deoxyfructose and 3-Deoxyglucosone in Human Urine and Plasma: Evidence for intermediate Stages of the Maillard Reaction in Vivo", Archives of Biochem. and Biophysics, 294: 130-137 (1992).
Reddy et al., "Ne-(Carboxymethyl)lysine is a Dominant Advanced Glycation End Product (AGE) Antigen in Tissue Proteins", Biochemistry, 34: 10872-10878 (1995).
Ikeda et al., "Ne-(Carboxymethyl)lysine Protein Adduct is a Major Immunological Epitope in Proteins Modified with Advanced Glycation End Products of the Maillard Reaction", Biochemistry, 35: 8075-8083 (1996).
Khalifah et al., "Kinetics of Nonenzymatic Glycation of Ribonuclease a Leading to Advanced Glycation End Products. Paradoxical Inhibition by Ribose Leads to Facile Isolation of Protein Intermediate for Rapid Post-Amadori Studies", Biochemistry, 35: 4645-4654 (1996).
Brownlee et al., "Advanced Glycosylation End Products in Tissue and the Biochemical Basis of Diabetic Complications", The New England Journal of Medicine, 318: 1315-1321 (1988).
Brownlee et al., "Glycation and Diabetic Complications", Diabetes, 43: 836-841 (1994).
Brownlee et al., "Glycation Products and the Pathogenesis of Diabetic Complications", Diabetes Care, 15: 1835-1843 (1992).
Niwa et al., "Elevated Serum Levels of 3-Deoxyglucosone, a Potent Protein-Cross-Linking Intermediate of the Maillard Reaction, in Uremic Patients", Nephron, 69: 438-443 (1995).
Dills et al., "Protein fructosylation: fructose and the Maillard reaction", Am. J. Clin. Nutr., 58(suppl): 779-S-87 (1993).
Yamada et al., "Increase in 3-Deoxyglucosone Levels in Diabetic Rat Plasma", J. Biol. Chem., 269: 20275-20280 (1994).
Takahashi et al., "In Vivo Glycation of Aldehyde Reductase, a Major 3-Deoxyglucosone Reducing Enzyme: Identification of Glycation Sites", 34: 1433-1438 (1995).
Fujii et al., "The Presence of 2-Keto-3-deoxygluconic Acid and Oxoaldehyde Dehydrogenase Activity in Human Erythrocytes", Biochem. Biophys. Res. Comm., 210: 852-857 (1995).
Barski et al., "Mechanism of Human Aldehyde Reductase: Characterization of the Active Site Pocket", Biochemistry, 34: 11264-11275 (1995).
Igaki et al., "Effects of 3-Deoxyglucosone on the Maillard Reaction", Clin. Chem., 36/4: 631-634 (1990).
Fox Chase Cancer Center Scientific Report, pp. 190-195 (1990-1991).
Fox Chase Cancer Center Scientific Report, pp. 214-217 (1991-1992).
Fox Chase Cancer Center Scientific Report, pp. 203-205 (1992-1993).
Fox Chase Cancer Center Scientific Report, pp. 175-178 (1993-1994).
Fox Chase Cancer Center Scientific Report, pp. 183-186 (1995).
Peterson et al., "Fructose metabolism in the human erythrocyte", Biochem. J., 284: 363-366 (1992).
Su et al., "Metabolism of Fructoselysine in the Kidney", Abstract presented at the International Society of Magnetic Resonance Meeting, Apr. 27-May 3, 1996.
Kappler et al., "Phosphorylated Amadori Products in Mammalian Kidneys", Abstract presented at the Maillard Symposium, Aug. 29-Sep. 1, 1993.
Brown et al., "Modulation of in vivo 3-deoxyglucosone levels", Biochem. Soc. Trans., 31(6): 1433-1437 (2003).
Takahashi et al., "Elevation of Aldose Reductase Gene Expression in Rat Primary Hepatoma and Hepatoma Cell Lines: Implication in Detoxification of Cytotoxic Aldehyes", Int. J. Cancer, 62: 749-754 (1995).
Melnick et al., "Aminoglycoside-induced Fanconi's syndrome", Am. J. Kidney Dis., 23(1): 118-22 (1994) [Abstract only].
Gainza et al., "Aminoglycoside-associated Fanconi's syndrome: an underrecognized entity", Nephron., 77(2): 205-11 (1997) [Abstract only].
Peppa et al., "Glucose, Advanced Glycation End Products, and Diabetes Complications: What is New and What Works", Clinical Diabetes, 21(4): 186-87 (2003).
Lal et al., "Fructose-3-Phosphate Production and Polyol Pathway Metabolism in Diabetic Rat Hearts", Metabolism, 46 (11): 1333-1338 (1997).
Fouda et al., "Effect of lipopolysaccharide on mitogen-activated protein kinases and cytosolic phospholipase A2", Biochem. J., 308: 815-822 (1995).
Bares et al., "Pancreatic cancer detected by positron emission tomography with 18F-labelled deoxyglucose: method and first results", Nucl. Med. Commun., 14(7): 596-601 (1993) [Abstract only].
Uchida et al., "Altered bile acid metabolism in nonobese, spontaneously diabetic (NOD) mice", Diabetes, 34(1): 79-83 (1985) [Abstract only].
Fournier et al., "Reactivity of lecithin-cholesterol acyl transferase (LCAT) towards glycated high-density lipoproteins (HDL)", Clinica Chimica Acta, 234: 47-61 (1995) [Abstract only].
Suzuki et al., "Assay of glycated fibrinogen in plasma as an indicator of blood glucose control", Rinsho. Byori, 38(3): 306-10 (1990).
Aoki et al., "Levels of fructosyllysine in collagen are low compared with the loss of lysine in diabetic rats: involvement of oxidation in creased cross-linking", Clin. Exp. Pharmacol. Physiol., 24(9-10): 657-60 (1997) [Abstract only].

* cited by examiner

METHODS FOR ALLEVIATING DELETERIOUS EFFECTS OF 3-DEOXYGLUCOSONE

CROSS-REFERENCE TO RELATED APPLICATIONS

The present application is a continuation of U.S. patent application Ser. No. 11/834,314, filed Aug. 6, 2007, now abandoned which is a continuation of U.S. patent application Ser. No. 11/478,497, filed Jun. 29, 2006, now abandoned which is a continuation of U.S. patent application Ser. No. 09/974,323, filed Oct. 10, 2001, now U.S. Pat. 7,071,298, which is a continuation-in-part of U.S. application Ser. No. 09/182,114, filed Oct. 28, 1998, now abandoned which is continuation-in-part of U.S. application Ser. No. 09/095,953, filed Jun. 11, 1998, now abandoned, which is a continuation-in-part of International Application No. PCT/US98/02192, filed Feb. 5, 1998, which is a continuation-in-part of U.S. application Ser. No. 08/794,433, filed Feb. 5, 1997, now U.S. Pat. No. 6,004,958. The entire disclosure of each of the aforesaid patent applications is incorporated by reference herein.

STATEMENT AS TO RIGHTS TO INVENTIONS MADE UNDER FEDERALLY-SPONSORED RESEARCH AND DEVELOPMENT

Pursuant to 35 U.S.C. §202(c), it is hereby acknowledged that the U.S. Government has certain rights in the invention described herein, which was made in part with funds from the National Institutes of Health (Grant Nos. DK44050, DK50317, DK50364, and DK55079).

BACKGROUND OF THE INVENTION

The present invention relates to therapeutic agents and their use for the treatment of diabetes, and in particular for preventing, reducing or delaying the onset of diabetic complications and other disorders of related etiology, such as glycogen storage diseases, including Fanconi's syndrome. More particularly, the present invention relates to a class of enzyme inhibitors which inhibit the enzymatic conversion of fructose lysine (FL) to fructose-lysine-3-phosphate (FL3P), which is believed to be an important step in the biochemical mechanism leading to diabetic complications. This invention also relates to a method of assessing a diabetic patient's risk of experiencing diabetic complications, as well as a method of determining the efficacy of therapeutic intervention in preventing, reducing or delaying the onset of diabetic complications.

There are four particularly serious complications of diabetes, namely, diabetic nephropathy or kidney disease; diabetic retinopathy which causes blindness due to destruction of the retina; diabetic neuropathy involving the loss of peripheral nerve function; and circulatory problems due to capillary damage. Both retinopathy and nephropathy are thought to be subsets of the general circulatory problems associated with this disease state. The role of microvascular dysfunction in late stage diabetes has been recently summarized (Tooke, Diabetes, 44: 721 (1995)). Throughout this disclosure, the terms "diabetes-associated pathologic conditions" and synonymous terms are meant to include the various well-known retinopathic, neuropathic, nephropathic, macroangiopathic, as well as other complications of diabetes and diseases of related etiology, including glycogen storage diseases.

The similarities between the pathologies arising from diabetes and those resulting from aging have been extensively reported. Studies have shown that many diabetes-associated pathologic conditions are clinically very similar to the pathologies normally associated with aging. It has been shown, for example, that in diabetes arteries and joints prematurely stiffen, lung elasticity and vital capacity prematurely decrease. Moreover, atherosclerosis, myocardial infarction and strokes occur more frequently in diabetics than in age-matched non-diabetic individuals. Diabetics are also more susceptible to infections, and are more likely to have hypertension, accelerated bone loss, osteoarthritis and impaired T-cell function at a younger age than non-diabetics.

The similarities between diabetes-associated pathologic conditions and aging would appear to suggest a common mechanistic rationale. A variety of mechanisms have been proposed as a common biochemical basis for both diabetes-associated pathologic conditions and aging. The hypothesis most strongly supported by data from human subjects is premised on a non-enzymatic glycosylation mechanism. This hypothesis states that the aging process and diabetes-associated pathologic conditions, such as those described above, are caused, at least in part, by protein modification and cross-linking by glucose and glucose-derived metabolites via the Maillard reaction (Monnier et al., Proc. Natl. Acad. Sci. USA, 81: 583 (1984) and Lee et al., Biochem. Biophys. Res. Comm., 123: 888 (1984)). The modified proteins resulting from such glycosylation reactions are referred to herein as advanced glycation end product-modified proteins (AGE-proteins). It is widely accepted that 3-deoxyglucosone (3DG) is a key intermediate in the multi-step reaction sequence leading to AGE-protein formation. 3DG is a glucose-derived metabolite that can react with proteins leading to the cross-linking of both intracellular and extracellular proteins, such as collagen and basement membranes.

In the case of diabetic complications, the reactions that lead to AGE-proteins are thought to be kinetically accelerated by the chronic hyperglycemia associated with this disease. Evidence supporting this mechanism includes data showing that long-lived proteins such as collagen and lens crystallins from diabetic subjects contain a significantly greater AGE-protein content than do those from age-matched normal controls. Thus, the unusual incidence of cataracts in diabetics at a relatively early age is explainable by the increased rate of modification and cross-linking of lens crystalline. Similarly, the early onset of joint and arterial stiffening, as well as loss of lung capacity observed in diabetics is explained by the increased rate of modification and cross-linking of collagen, the key structural protein. Because these proteins are long-lived, the consequences of modification tend to be cumulative.

Another factor demonstrating cause and effect relationship between diabetic complications and hyperglycemia is hyperglycemic memory. One particularly striking example of this phenomenon is the development of severe retinopathy in dogs that were initially diabetic, then treated to restore normal blood glucose levels. Although the dog eyes were histologically normal at the time of the treatment, over time diabetic retinopathy developed in these animals in spite of the normalized glucose concentrations (Engerman et al., Diabetes, 36: 808 (1987)). Thus, the underlying damage to the eyes irreversibly occurred during the period of early hyperglycemia, before clinical symptoms were evident.

Diabetic humans and animals have been shown to have higher than normal concentrations of early and late sugar modified AGE-proteins. In fact, the increase in AGE-proteins is greater than the increase in blood glucose levels. The concentration of AGE-proteins can be estimated by fluorescence measurement, as some percentage of sugar molecules rearrange to produce protein-bound fluorescent molecules.

The pathogenic role of AGE-proteins is not limited to diabetes. Protein glycation has been implicated in Alzheimer's disease (Harrington et al., Nature, 370: 247 (1994)). Increased protein fluorescence is also seen with aging. Indeed, some theories trace the aging process to a combination of oxidative damage and sugar-induced protein modification. Thus, a therapy that reduces AGE-protein formation may also be useful in treating other etiologically-similar human disease states, and perhaps slow the aging process.

It has generally been assumed that the formation of AGE-proteins begins with the reaction of a protein amino group and a sugar, primarily glucose. One typical literature citation states "The initial adduct formed by glycation of $\epsilon$-amino groups of lysine residues is the Amadori compound, fructoselysine. Glycation is an initial step in a complex series of reactions, known collectively as the Maillard or browning reaction, which ultimately leads to the formation of crosslinked, precipitated, oxidized, brown and fluorescent proteins". K. J. Knecht et al., Archives of Biochem. Biophys., 294: 130 (1992).

The formation of AGE-proteins from sugars is a multi-step process, involving early, reversible reactions with sugars to produce fructose-lysine containing proteins. These modified proteins then continue to react to produce irreversibly modified AGE-proteins. It is clear that AGE-proteins are not identical to proteins containing glycated-lysine residues, as antibodies raised against AGE-proteins do not react with fructose-lysine. It is also clear that AGE-proteins exist as multiple chemical species; however few have been identified. The chemical species E-Amino-(carboxymethyl)lysine has been identified as one important final AGE-protein structure in recent studies (Reddy et al., Biochem., 34: 10872 (1995) and Ikeda et al., Biochemistry, 35: 8075 (1996)). This study failed to chemically identify another AGE-protein epitope that made up approximately 50% of the modified sites. A method of studying the kinetics of AGE-protein formation from ribose has recently been developed (Khalifah et al., Biochemistry, 35: 4645 (1996)). However, this study suggests that ribose may play an important physiological role in AGE-protein formation, supporting the relatively broad definitions of glycated-lysines and fructose-lysine provided below.

Other references point out the distinction between proteins containing glycated lysine residues and AGE proteins, "Equilibrium levels of Schiff-base and Amadori products are reached in hours and weeks, respectively. The reversible, equilibrium nature of early glycosylation products is important, because it means that the total amount of such products, even on very long-lived proteins, reaches a steady-state plateau within a short period of time. Since these early glycosylation products do not continue to accumulate on collagen and other stable tissue proteins over years in chronic diabetes, it is not surprising that their concentration does not correlate with either the presence or the severity of diabetic retinopathy . . . . Some of the early glycosylation products on collagen and other long-lived proteins of the vessel walls do not dissociate, however. Instead, they undergo a slow, complex series of chemical rearrangements to form irreversible advanced glycosylation end products". M. Brownlee et al., New England Journal of Medicine, 318: 1315 (1988). The only route for production of these modified proteins which is described in the scientific literature involves an initial reaction between proteins and sugar molecules.

Numerous references point out that the formation of AGE-proteins occurs through a multi-step pathway and that 3-deoxyglucosone (3-DG) is a key intermediate in this pathway. M. Brownlee, Diabetes, 43: 836 (1994); M. Brownlee, Diabetes Care, 15: 1835 (1992); T. Niwa et al., Nephron, 69: 438 (1995); W. L. Dills, Jr., Am. J. Clin. Nutr., 58: 5779 (1993); H. Yamadat et al., J. Biol. Chem., 269: 20275 (1994); N. Igaki et al., Clin. Chem., 36: 631 (1990). The generally accepted pathway for formation of 3DG from the reaction of sugars and proteins is illustrated in FIG. 1. As can be seen in FIG. 1, a sugar (glucose) molecule initially forms a Schiff base with a protein-lysine amino group (I). The resulting Schiff base then rearranges to produce fructose-lysine modified proteins (II). The reactions leading up to (II) are freely reversible. (II) can rearrange to produce 3DG and free protein lysine. Subsequent reaction between 3DG and protein is the first irreversible step in AGE-protein formation.

Insofar as is known, it has never been reported that 3DG can be produced by alternative pathways, or indeed, that the major source of 3-DG is from an enzyme catalyzed metabolic pathway, rather than from the uncatalyzed reactions shown in FIG. 1.

Diabetic patients have significantly more 3DG in serum than do non-diabetic patients (12.78±2.49 μM versus 1.94±0.17 μM). (Toshimitsu Niwa et al., Nephron, 69: 438 (1995)). Nonetheless, this toxic compound is found in normal healthy individuals. Thus, it is not surprising that the body has developed a detoxification pathway for this molecule. One of these reactions is catalyzed by aldehyde reductase which detoxifies 3DG by reducing it to 3-deoxyfructose (3DF) which is efficiently excreted in urine (Takahashi et al., Biochem, 34: 1433 (1995)). Another detoxification reaction oxidizes 3DG to 3-deoxy-2-ketogluconic acid (DGA) by oxaldehyde dehydrogenase (Fujii et al., Biochem. Biophys. Res. Comm., 210: 852 (1995)).

Results of studies to date show that the efficiency of at least one of these enzymes, aldehyde reductase, is adversely affected in diabetes. When isolated from normal rat liver, a fraction of this enzyme is partially glycated on lysines 67, 84 and 140 and has a low catalytic efficiency when compared with the normal, unmodified enzyme (Takahaski et al., Biochem., 34: 1433 (1995)). Since diabetic patients have higher ratios of glycated proteins than normoglycemic individuals they are likely to have both higher levels of 3DG and a reduced ability to detoxify this reactive molecule by reduction to 3DF.

The mechanism of aldehyde reductase has been studied. These studies determined that this important detoxification enzyme is inhibited by aldose reductase inhibitors (ARIs) (Barski et al., Biochem., 34: 11264 (1995)). ARIs are currently under clinical investigation for their potential to reduce diabetic complications. These compounds, as a class, have shown some effect on short term diabetic complications. However, they lack clinical effect on long term diabetic complications and they worsen kidney function in rats fed a high protein diet. As will appear hereinbelow, this finding is consistent with the newly discovered metabolic pathway for lysine recovery underlying the present invention. A high protein diet will increase the consumption of fructose-lysine, which undergoes conversion into 3DG by the kidney lysine recovery pathway. The detoxification of the resulting 3DG by reduction to 3DF will be inhibited by ARIs therapy, which consequently leads to an increase in kidney damage, as compared to rats not receiving ARIs. This is because inhibition of the aldose reductase by the ARIs would reduce availability of aldose reductase for reducing 3DG and 3DF.

The role of 3-DG in contributing to human disease has been previously investigated as will be appreciated from a review of the patents summarized below.

U.S. Pat. No. 5,476,849 to Ulrich et al. describes a method of inhibiting the formation of AGE-proteins using aminobenzoic acids and derivatives. These compounds presumably act by reacting with 3-DG and removing it from the system before it can react with proteins to begin the irreversible steps of AGE-protein formation.

U.S. Pat. Nos. 4,798,583 and 5,128,360 to Cerami et al. describes the use of aminoguanidine to prevent AGE-protein formation and diabetes-induced arterial wall protein crosslinking. Aminoguanidine was shown to react with an early glycosylation product. This early product is 3DG, as defined herein. These patents do not contemplate the possibility of inhibiting the formation of 3-DG. They focus exclusively on complexing this toxic molecule.

U.S. Pat. No. 5,468,777 to France et al. describes methods and agents for preventing the staining of teeth caused by the non-enzymatic browning of proteins in the oral cavity. Cysteine and cysteine derivatives are described as particularly useful in this application.

U.S. Pat. No. 5,358,960 to Ulrich et al. describe a method for inhibiting AGE-protein formation using aminosubstituted imidazoles. These compounds were shown to react with an early glycosylation product (3DG). No mention is made in this patent that a metabolic source of 3DG may exist. This patent envisions that 3DG is made exclusively as an intermediate in the non-enzymatic browning of proteins.

U.S. Pat. No. 5,334,617 to Ulrich et al. describes amino acids useful as inhibitors of AGE-protein formation. Lysine and other bifunctional amino acids are described as particularly useful in this regard. These amino acids are described as reacting with the early glycosylation product from the reaction of glucose and proteins. It appears that the early glycosylation product described in this patent is 3DG.

U.S. Pat. No. 5,318,982 to Ulrich et al. describes the inhibition of AGE-protein formation using as the inhibitory agent 1,2,4-triazoles. The inhibitors described in this patent contain diamino-substituents that are positioned to react with and complex 3DG. The patent describes these compounds as reacting with an early glycosylation product (3DG as defined herein).

U.S. Pat. No. 5,272,165 to Ulrich et al. describes the use of 2-alkylidene-aminoguanidines as inhibitors of AGE-protein formation. The inhibitors described in this patent are said to be highly reactive with 3DG. No mention is made of inhibiting the metabolic formation of 3DG in this patent.

U.S. Pat. No. 5,262,152 to Ulrich et al. describes the use of amidrazones and derivatives to inhibit AGE-protein formation. The compounds described in this patent are α-effect amines. W. P. Jencks, 3rd ed., McGraw Hill, New York. Compounds of this category are known to react with dicarbonyl compounds, e.g. 3DG.

U.S. Pat. No. 5,258,381 to Ulrich et al. describes the use of 2-substituted-2-imidazolines to inhibit AGE-protein formation. The compounds described in this patent contain adjacent amino groups that can readily react with 3DG.

U.S. Pat. No. 5,243,071 to Ulrich et al. describes the use of 2-alkylidene-aminoguanidies to inhibit AGE-protein formation. The compounds described in this patent are highly reactive with 3DG and function by complexing this reactive, toxic molecule.

U.S. Pat. No. 5,221,683 to Ulrich et al. describes the use of diaminopyridine compounds to inhibit AGE-protein formation. The diaminopyridine compounds described as particularly useful will react with 3DG to form a stable, six-member ring containing complex.

U.S. Pat. No. 5,130,337 to Ulrich et al. describes the use of amidrazones and derivatives to inhibit AGE-protein formation. The inhibitors described in this patent are α-effect amines which, as is know in the art, will rapidly react with 3DG and form stable complexes.

U.S. Pat. No. 5,130,324 to Ulrich et al. describes the use of 2-alkylidene-aminoguanidines to inhibit AGE-protein formation. The compounds described in this patent function by reacting with the early glycosylation product resulting from the reaction of glucose with proteins (3DG).

U.S. Pat. No. 5,114,943 by Ulrich et al. describes the use of amino-substituted pyrimidines to inhibit AGE-protein formation. The compounds described in this patent are said to rapidly react with and detoxify 3DG.

None of the above-mentioned patents suggest inhibition of the metabolic formation of 3DG as a means of therapeutic intervention to prevent diabetic complications. Indeed, none of these patents even suggest the involvement of an enzymatic pathway in the production of 3DG.

U.S. Pat. No. 5,108,930 to Ulrich et al. describes a method for detecting the levels of aminoguanidine in biological samples. This assay is described as having potential utility in determining kidney function by measuring the aminoguanidine elimination time. The principal utility intended for the assay method described in this patent is in the measurement of tissue levels of aminoguanidine, so that doses sufficient to inhibit AGE-protein formation can be maintained in animal and human studies. No mention is made in this patent of using urine 3DG, 3DF or DGA ratios to determine diabetics at risk for complications.

U.S. Pat. No. 5,231,031 to Szwergold et al. describes a method for assessing the risk of diabetic-associated pathologic conditions and determining the efficacy of therapies for these complications. This patent describes the measurement of two phosphorylated compounds in erythrocytes of diabetic patients. These two compounds were not chemically identified in this patent. However, neither compound is 3DG or 3DF, whose levels are measured in urine in the diagnostic embodiment of the present invention.

Methods for monitoring metabolic control in diabetic patients by measurement of glycosylation end-products are known. The concentration of glycosylated hemoglobin is known to reflect mean blood glucose concentration during the preceding several weeks. U.S. Pat. No. 4,371,374, issued to A. Cerami et al., describes a method for monitoring glucose levels by quantitation of the degradation products of glycosylated proteins, more specifically non-enzymatically glycosylated amino acids and peptides, in urine. This method purports to utilize the affinity of alkaline boronic acids for forming specific complexes with the coplanar cis-diol groups found in glycosylation end-products to separate and quantitate such end-products.

U.S. Pat. No. 4,761,368 issued to A. Cerami describes the isolation and purification of a chromophore present in browned polypeptides, e.g., bovine serum albumin and poly-L-lysine. The chromophore, 2-(2-furoyl)-4(5)-2(furoyl)-1H-imidazole (FFI) is a conjugated heterocycle derived from the condensation of two molecules of glucose with two lysine-derived amino groups. This patent further describes the use of FFI in a method for measuring "aging" (the degree of advanced glycosylation) in a protein sample wherein the sample "age" is determined by measuring the amount of the above-described chromophore in the sample and then comparing this measurement to a standard (a protein sample having an amount of FFI which has been correlated to the "age" of the sample).

Without wishing to be bound by any theory, it is believed that the present invention may be used to treat any glycogen storage disease. Glycogen storage diseases (glycogenoses or GSDs) are hereditary disorders in which a patient is missing one or more of the enzymes that interconvert sugar and glycogen. The GSDs that are presently known are classified as Types 0 to VII, depending on the identity of the missing enzyme or enzymes, and are also known by common names including von Gierke's disease, Pompe's disease, Forbes' disease, Andersen's disease, McArdle's disease, Hers' disease, and Tarui's disease. Fanconi's syndrome is also believed to be a glycogen storage disease, and, as such, amenable to treatment with compounds of the present invention.

There is a long-standing, unfilled need in existing treatment regimens of diabetic patients for effective means to identify those at risk of developing diabetes-associated pathologic conditions, to prevent, reduce or delay the onset of such conditions by therapeutic intervention and to determine the benefit of such therapeutic intervention. A parallel need exists in the treatment regimens of patients affected with glycogen storage diseases, including Fanconi's syndrome.

SUMMARY OF THE INVENTION

The present invention arose from the discovery of a metabolic pathway that involves the enzyme-mediated conversion of FL to FL3P and produces relatively high concentrations of 3-deoxyglucosone (3DG) in organs affected by diabetes. Subsequent research into the biochemical function of this newly discovered pathway tends to indicate that it has an important role in the etiology of diabetic kidney disease. It is also suspected that this pathway contributes to the development of the various known diabetes-associated pathologic conditions.

This discovery has found practical application in the present invention which, in one aspect, provides a class of compounds which have enzyme inhibitory activity and are effective to inhibit the enzymatic conversion of fructose-lysine to fructose-lysine-3-phosphate. The relevant enzyme inhibitory activity of the compounds of the present invention is readily determinable by assay. The assay method comprises providing an aqueous solution of fructose-lysine, adenosine triphosphate (ATP), a source of fructose-lysine-3-phosphate kinase and a compound of the present invention in an amount sufficient to demonstrate inhibitory activity, subjecting the resulting solution to conditions promoting the formation of fructose-lysine-3-phosphate and adenosine diphosphate as products of the interaction of the above-mentioned kinase, fructose-lysine and adenosine triphosphate, and measuring the production of at least one of such products, the compounds of the present invention reducing the amount of such products, as compared to an aqueous solution of the same relative amounts of fructose-lysine, adenosine triphosphate and source of fructose-lysine-3-phosphate kinase, without the addition of a compound of the present invention. The assay method just described is also within the scope of the present invention.

According to another aspect, the present invention provides a pharmaceutical preparation for preventing, reducing or delaying the onset of diabetic complications in a diabetic patient, comprising, as an active agent, a compound of the invention, as described above, and a pharmaceutically acceptable vehicle.

According to a further aspect of the present invention, there is provided a method for preventing, reducing or delaying the onset of diabetic complications in a patient at risk of developing same, which method comprises administering to the patient a compound of the present invention in an amount effective to inhibit the enzymatic conversion of fructose-lysine to fructose-lysine-3-phosphate. This same method may be used for the prevention or treatment of other etiologically-similar disease states, as will be further described hereinbelow.

According to still another aspect, the present invention provides a method for assessing a diabetic patient's risk of experiencing a diabetes-associated pathologic condition. This method comprises administering to the patient a source of glycated-lysine residues in an amount providing a predetermined dose of the glycated-lysine residues, and measuring the ratio of 3-deoxyglucosone to 3-deoxyfructose in a biological sample obtained from the patient, with reference to the ratio of 3-deoxyglucosone to 3-deoxyfructose in a normal subject, i.e., a non-diabetic subject or one having no clinical symptoms of diabetes. The higher ratio of 3-deoxyglucosone to 3-deoxyfructose in the diabetic patient sample, in comparison to that of the asymptomatic subject is indicative that the diabetic patient is at higher risk of experiencing a diabetes-associated pathologic condition.

The present invention also provides a method for assessing the efficacy of therapeutic intervention in preventing diabetic complications. The method involves measuring the concentration of 3-deoxyglucosone, 3-deoxyfructose and fructose-lysine in biological samples obtained from a diabetic patient, both before and after initiation of the therapeutic intervention. The sum of the 3-deoxyglucosone and 3-deoxyfructose concentrations are then compared to the concentration of fructose-lysine in the samples. A decrease in the sum of 3-deoxyglucosone and 3-deoxyfructose concentrations relative to the fructose-lysine concentration in the biological sample taken after initiation of therapeutic intervention, as compared to the same concentrations measured in the biological sample taken before initiation of the therapeutic intervention, is indicative of the efficacy of the therapeutic intervention.

As yet another aspect of the present invention, there is provided a method for apprising a diabetic person of the potential of a food product to contribute to the development of a diabetic-associated pathologic condition. This method involves measuring the content of glycated-lysine residues in the food product and providing this information to diabetic patients, e.g., on the package of the food product or in a publication intended for use by diabetics. In research leading up to the present invention, it has been discovered that elevated levels of 3DF in biological samples, e.g., urine, are associated with a significant risk of developing diabetic complications. Thus, a method has been provided for assessing a diabetic patient's risk of experiencing a diabetes-associated pathologic condition based on measurement of the 3DF present in a biological sample of a diabetic patient with reference to one or more predetermined baseline levels of 3DF as an indicator of the likelihood that the patient will develop diabetic complications, or not.

Other related research led to the discovery of a method of reducing susceptibility to carcinoma in a patient associated with the intake of glycated proteins. The method comprises the administration of a pharmaceutical composition which contains an active compound having inhibitory activity for the enzymatic conversion of fructose-lysine to fructose-lysine-3-phosphate. Also embodied in the present invention is a method of preventing, reducing, or delaying the onset of carcinoma caused by the formation of AGE-proteins. The method comprises administering a therapeutic amount of an agent that inhibits production of 3-deoxyglucosone.

As a means to further assess the molecular mechanism of malignant transformation associated with administration of a diet containing glycated proteins, a method for inducing carcinoma in a susceptible test animal has been discovered which comprises feeding the animal with a glycated protein diet for a sufficient time period, such that 3-deoxyglucosone is elevated in biological fluids at least three fold. Such animals would be assessed relative to untreated control animals.

A method of screening for substances which affect the development of carcinoma has also been discovered. Carcinoma will be induced in test animals via feeding of glycated protein diet such that 3DG levels are elevated at least 3 fold in biological fluids. The animals are then divided into two groups, one of which will receive the compound to be assessed, while the other group serves as a negative control. After a suitable time period, both groups of animals will be sacrificed and the presence and/or absence of carcinoma in both groups assessed.

Finally, another method for screening for substances which prevent, reduce or delay the onset of carcinoma comprises the steps of feeding susceptible test animals a glycated protein diet in an amount and for a time sufficient to maintain 3-deoxyglucosone (3DG) content of a biological fluid elevated at least 3-fold relative to the 3DG content of a biological fluid from a similar susceptible test animal fed a diet substantially free of the glycated protein. A test substance will then be administered to one portion of the test animals but not to the other portion. The animals will then be sacrificed and tissue sections compared from each such portion of susceptible test animals to assess the effects of the test substance.

DETAILED DESCRIPTION OF THE INVENTION

Figure 1:
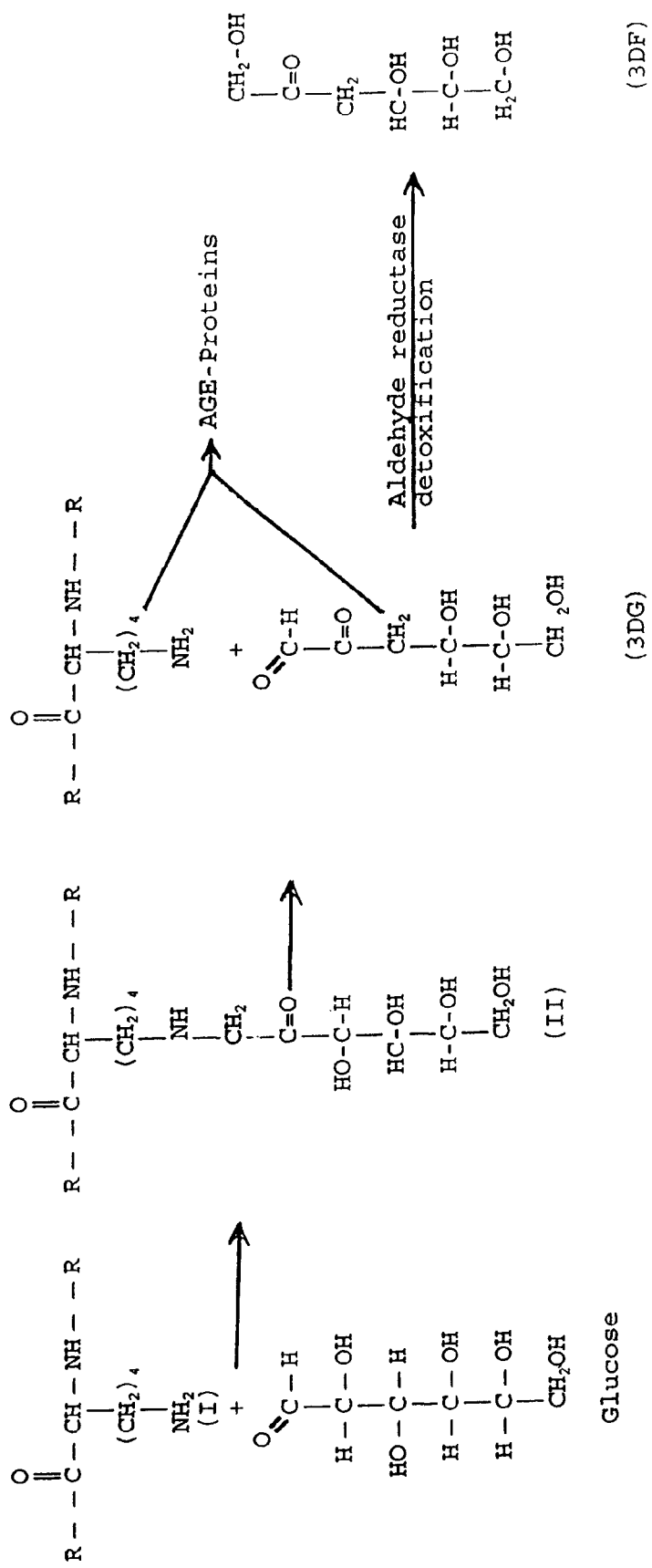
FIG. 1 shows the initial step involved in the multi-step reaction leading to irreversibly-modified AGE-proteins.

The following definitions are provided to facilitate understanding of the present invention, as described in further detail hereinbelow:

1. Glycated-Lysine Residues—The expression "glycated lysine residues", as used herein, refers to the modified lysine residue of a stable adduct produced by the reaction of a reducing sugar and a lysine-containing protein.

The majority of protein lysine residues are located on the surface of proteins as expected for a positively charged amino acid. Thus, lysine residues on proteins which come in contact with serum, or other biological fluids, can freely react with sugar molecules in solution. This reaction occurs in multiple stages. The initial stage involves the formation of a Schiff base between the lysine free amino group and the sugar keto-group. This initial product then undergoes the Amadori rearrangement, to produce a stable ketoamine compound.

This series of reactions can occur with various sugars. When the sugar involved is glucose, the initial Schiff base product will involve imine formation between the aldehyde moiety on C-1 of the glucose and the lysine ϵ-amino group. The Amadori rearrangement will result in formation of lysine coupled to the C-1 carbon of fructose, 1-deoxy-1-(ϵ-aminolysine)-fructose, herein referred to as fructose-lysine or FL.

Similar reactions will occur with other aldose sugars, for example galactose and ribose (Dills, Am. J. Clin. Nutr., 58: S779 (1993)). For the purpose of the present invention, the early products of the reaction of any reducing sugar and the ϵ-amino residue of protein lysine are included within the meaning of glycated-lysine residue, regardless of the exact structure of the modifying sugar molecule.

Also, the terms glycated-lysine residue, glycated protein and glycosylated protein or lysine residue are used interchangeably herein, which is consistent with current usage in scientific journals where such expressions are often used interchangeably.

2. Fructose-lysine—The term "fructose-lysine" (FL) is used herein to signify any glycated-lysine, whether incorporated in a protein/peptide or released from a protein/peptide by proteolytic digestion. This term is specifically not limited to the chemical structure commonly referred to as fructose-lysine, which is reported to form from the reaction of protein lysine residues and glucose. As noted above, lysine amino groups can react with a wide variety of sugars. Indeed, one report indicates that glucose is the least reactive sugar out of a group of sixteen (16) different sugars tested (Bunn et al., Science, 213: 222 (1981)). Thus, tagatose-lysine formed from galactose and lysine, analogously to glucose is included wherever the term fructose-lysine is mentioned in this description, as is the condensation product of all other sugars, whether naturally-occurring or not. It will be understood from the description herein that the reaction between protein-lysine residues and sugars involves multiple reaction steps. The final steps in this reaction sequence involve the crosslinking of proteins and the production of multimeric species, known as AGE-proteins, some of which are fluorescent. Proteolytic digestion of such modified proteins does not yield lysine covalently linked to a sugar molecule. Thus, these species are not included within the meaning of "fructose-lysine", as that term is used herein.

3. Fructose-lysine-3-phosphate—This compound is formed by the enzymatic transfer of a high energy phosphate group from ATP to FL. The term fructose-lysine-3-phosphate (FL3P), as used herein, is meant to include all phosphorylated fructose-lysine moieties that can be enzymatically formed whether free or protein-bound.

4. Fructose-lysine-3-phosphate kinase—This term refers to one or more proteins which can enzymatically convert FL to FL3P, as defined above, when additionally supplied with a source of high energy phosphate.

5. 3-Deoxyglucosone-3-Deoxyglucosone (3DG) is the 1,2-dicarbonyl-3-deoxysugar (also known as 3-deoxyhexylosone) which is formed upon breakdown of FL3P to yield free lysine and inorganic phosphate. For purposes of the present description, the term 3-deoxyglucosone is intended to include all possible dicarbonyl sugars which are formed upon breakdown of FL3P, having the broad definition of FL3P stated above.

6. FL3P Lysine Recovery Pathway—A lysine recovery pathway exists in human kidney, and possibly other tissues, which regenerates unmodified lysine as a free amino acid or incorporated in a polypeptide chain. As will be further explained below, this pathway is an important factor contributing to the complications of diabetes.

7. AGE-Proteins—The term "AGE-proteins" (Advanced Glycation End-product modified proteins) has been used in scientific journals, and is used herein, to refer to the final product of the reaction between sugars and proteins (Brownlee, Diabetes Care, 15: 1835 (1992) and Niwa et al., Nephron, 69: 438 (1995)). It is clear that the reaction, for example, between protein lysine residues and glucose does not stop with the formation of fructose-lysine. FL can undergo multiple dehydration and rearrangement reactions to produce non-enzymatic 3DG, which reacts again with free amino groups, leading to cross-linking and browning of the protein involved. Indeed, there is reasonable evidence that 3DG, as defined hereinabove, is a central intermediate in this modification reaction.

8. "Glycated Diet"—As used herein, this expression refers to any given diet in which a percentage of normal protein is replaced with glycated protein. The expression "glycated diet" and "glycated protein diet" are used interchangeably herein.

At least some, and possibly all, of the complications of diabetes are due to the covalent modification of proteins by glucose and other reactive sugars. M. Brownlee, Diabetes, 43: 836 (1994). As noted above, diabetic humans and animals have been shown to have higher concentrations of sugar modified proteins than normal. In fact, the increase in diabetes-associated AGE-proteins is greater than the increase in blood glucose levels.

Previously, it had been generally accepted that the origin of 3DG in vivo was from the decomposition of proteins containing glycated lysine residues. It had also been commonly believed that these glycated-lysines could not be used as an amino acid source. As will appear hereinbelow, this previous belief was incorrect.

9. "Susceptible test animal"—As used herein this expression refers a strain of laboratory animals which, due to the presence of certain genetic mutations, have a higher propensity towards malignant transformation and tumor formation. Unless otherwise specified, the Eker rat which has a mutation in the tuberous sclerous gene (Tsc-2) was utilized in the studies described herein. One of ordinary skill in the art is aware of a variety of other laboratory rat or mouse strains with increased propensity for tumor formation. The phrase "similar susceptible test animal" refers to animals of a comparable genetic background which are used as control, untreated animals.

As mentioned above, the present invention evolved from the discovery of a previously unknown metabolic pathway which produces 3DG in an enzyme-catalyzed reaction. This enzymatic pathway is capable of enzymatic inhibition, thereby reducing the production of toxic 3DG.

During the course of a series of studies on diabetic kidneys, examination of $^{31}P$ NMR spectra from perchloric acid extracts of kidneys from streptozotoxin induced diabetic rats revealed an unusual new peak in the NMR spectrum. Previous studies by the present inventors had demonstrated the presence of fructose-3-phosphate in rat lens and human erythrocytes (A. Petersen et al., Biochem. J., 284: 363-366 (1992); Lal et al., Arch. Biochem. Biophys., 318: 191 (1995); Szwergold et al., Science, 247: 451 (1990) and Lal et al., Investigative Opthalmology and Visual Science, 36(5): 969 (1995)). Earlier studies had identified other unusual phosphorylated sugars in rat lens (Szwergold et al., Diabetes, 44: 810 (1995) and Kappler et al., Metabolism, 44: 1527 (1995)). Thus it was reasonable to assume that this newly identified peak was another phosphorylated sugar. Further extensive laboratory investigation revealed that this new compound was not a simple sugar, but rather fructose-lysine phosphorylated on the 3 position of the fructose component.

This identification was confirmed in two ways. Authentic fructose-lysine-3-phosphate (FL3P) was synthesized by the procedure disclosed in Example 2, below, and shown to co-resonate in the $^{31}P$ NMR spectrum with the peak in diabetic rat kidneys. Synthetic fructose-lysine was also injected into non-diabetic rats. These rats showed a substantial increase in the levels of FL3P in their kidneys following this injection.

Two experiments were conducted to demonstrate that FL3P is derived directly from FL in an enzyme catalyzed reaction. Fructose-lysine labeled with deuterium at the C3 position of the fructose moiety was synthesized and injected into rats. Three hours after injection, the kidneys of these rats were removed and extracted with perchloric acid. NMR spectroscopy revealed that the FL3P material isolated from these rats contained the deuterium label at the C3 position of the fructose moiety. In addition, rat kidney homogenates demonstrate the ability to produce FL3P in a reaction requiring both ATP and fructose-lysine. This last-mentioned experiment confirms the presence of a specific FL3P kinase, as no FL3P is formed when only fructoselysine and ATP are incubated together under physiological conditions. Further experiments which involved the fractionation of kidney cortex have demonstrated that this kinase activity is not distributed uniformly in the kidney but is concentrated in the proximal tubular region, which is one of the earliest anatomical sites to demonstrate damage in human and animal diabetic kidneys.

FL3P is not stable in aqueous solution. It rapidly degrades to form 3DG, lysine and inorganic phosphate. This reaction also occurs in vivo. It is not currently know if the degradation of FL3P in vivo is a spontaneous or enzyme catalyzed reaction. It is strongly suspected, however, that enzymatic catalysis is involved, as the production of 3DG from fructose lysine occurs very rapidly in intact kidney.

Figure 2:
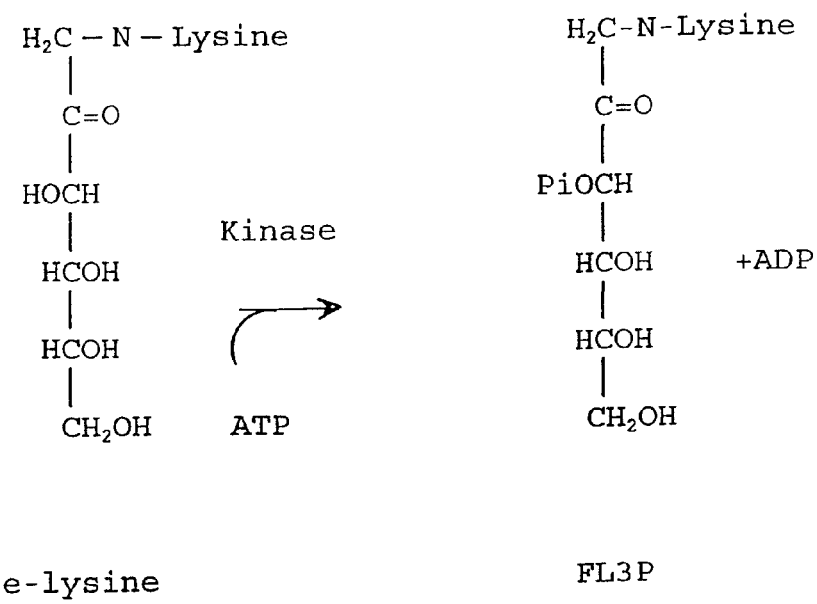
FIG. 2 illustrates the reactions involved in the lysine recovery pathway.
Figure 2:
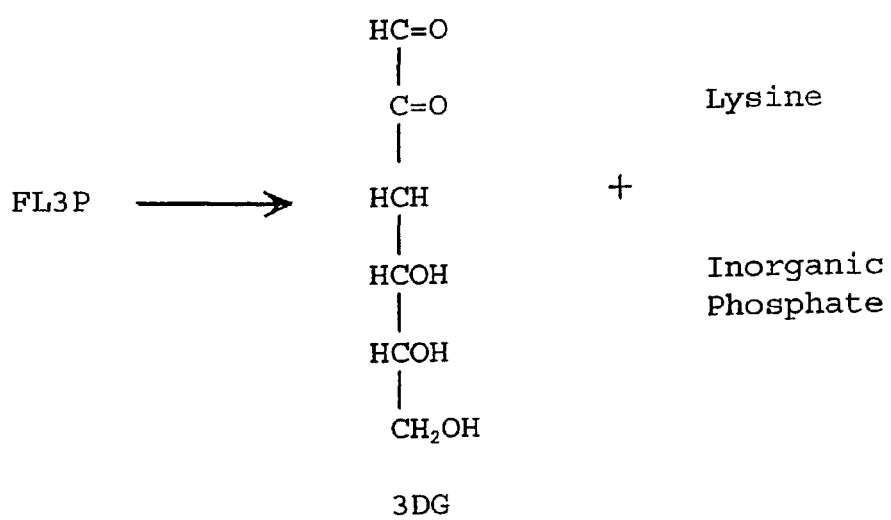

The reaction steps in the FL3P lysine recovery pathway are presented in FIG. 2. In the first step, fructose-lysine and ATP react to form fructose-lysine-3-phosphate (FL3P) and ADP in a reaction catalyzed by FL3P kinase. Phosphorylation occurs on the 3-position of the fructose moiety, leading to destabilization of the fructoselysine molecule. The resulting FL3P then decomposes to form 3-deoxyglucosone (3DG), inorganic phosphate, and unmodified, free, reusable lysine, which is available for utilization in protein synthesis. Aldehyde reductase detoxifies 3DG by reduction to 3-deoxyfructose (3DF), which is excreted in urine.

Although FIG. 2 illustrates this pathway using the most prevalent glycated-lysine, fructose-lysine, it will be readily apparent to those skilled in the art that a wide variety of similar molecules can flux through this pathway. Indeed, as will be explained in further detail below, the substrate selectivity of the FL3P lysine recovery pathway is quite broad, warranting the broad definition of the terms given above.

Additional experiments have shown that the lysine recovery pathway is found in a wide variety of animal species, including sheep, pig, dog, rabbit, cow, mice and chicken. This pathway is also present in humans. The ubiquitous presence of the FL3P lysine recovery pathway can be understood, given that lysine is an essential amino acid which is present in relatively low concentrations in most foods. In addition, an appreciable percentage of the lysine residues in food will exist in the glycated form and the proportion of this modified lysine will increase when the food is cooked. Since these glycated lysine residues can not be utilized for protein synthesis, a recovery pathway for lysine is of great utility and affords a selective advantage to organisms which possess it.

Figure 7A:
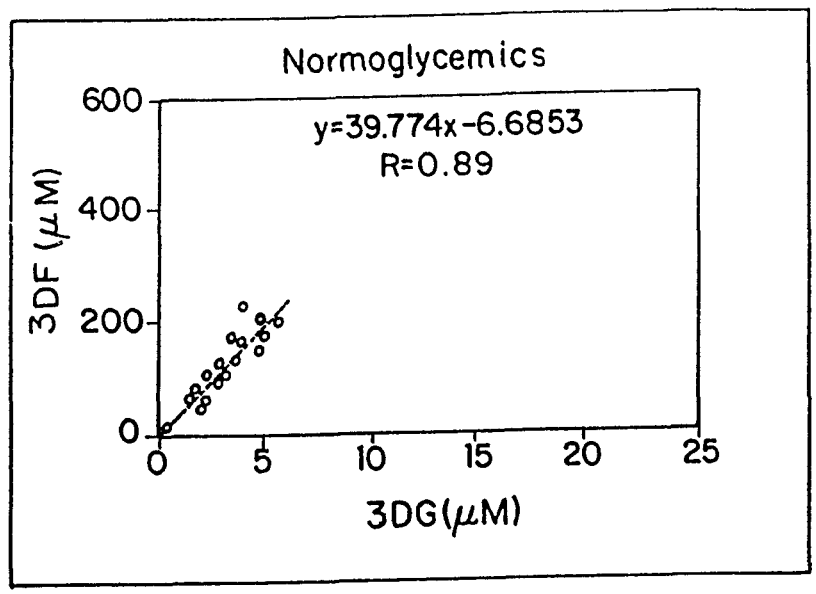
FIGS. 7A and 7B are graphical representations of fasting levels of 3DG in the urine of normals and diabetic patients plotted against the fasting level of 3DF.
Figure 7B:
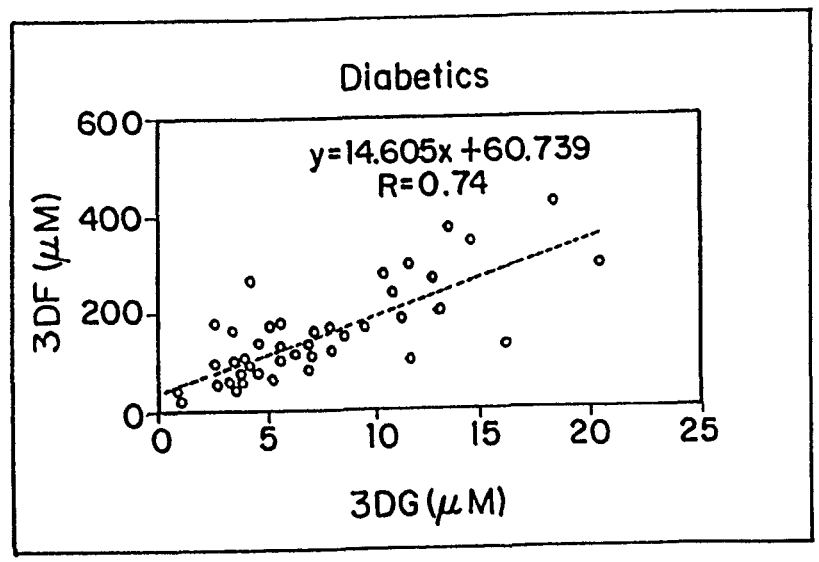

Diabetes has two effects on the lysine recovery pathway. Blood proteins contain higher concentrations of glycated-lysines when isolated from diabetics than from non-diabetic-individuals. Thus, diabetics are subject to greater flux through the lysine recovery pathway than non-diabetics. Additionally, from preliminary observations on the ratios of 3DG and 3DF in the urine of diabetics and normals, diabetics appear to have a reduced ability to detoxify 3DG that is produced via this pathway. These two factors combine to produce higher urinary concentrations of 3DG in diabetics (See FIG. 7; also Lal et al., Arch. Biochem. and Biophys., 342(1): 254-60 (1997).

The agents involved in the lysine recovery pathway have been identified in other tissues besides kidney, specifically red blood cells, lens, and peripheral nerve tissues. All of these tissues are affected by the complications of diabetes. The location in red blood cells correlates with the microvascular complications of diabetes, e.g., diabetic retinopathy, the kidney location correlates with diabetic nephropathy, while the location in peripheral nerve correlates with diabetic peripheral neuropathy. These agents are also found in pancreas. Experiments are in progress to determine the presence of these agents in skin. If found to be present, it is believed that their deleterious effects may be ameliorated by a topical treatment using the inhibitory compounds of the invention in a suitable vehicle to prevent collagen crosslinking, and thereby improve skin elasticity.

Experiments have been conducted that tend to prove that humans produce both 3DG and 3DF from orally ingested proteins containing glycated-lysine residues. These experiments, which are described in detail below, convincingly demonstrate that the lysine recovery pathway exists in humans. These experiments also shed light on a puzzling phenomenon, namely, that some diabetics develop diabetic complications, while others, even those in poor glycemic control, do not develop such complications. The reason for this phenomenon is apparent from the data presented herein. Diabetics have a differing ability to detoxify 3DG. A subset of the diabetic population appears to have relatively higher aldehyde reductase activities than does the majority of diabetics. Consequently, these individuals are capable of handling the increased flux through the lysine recovery pathway by efficiently detoxifying the higher than normal level of 3DG. Others with impaired capacity are less able to detoxify their elevated 3DG levels, and consequently are at higher risk of developing diabetic complications.

As will be described in more detail below, it has been experimentally demonstrated that stimulation of the lysine recovery pathway can occur through the use of a glycated protein diet. As was the case with FL above, elevation of FL3P, 3DG and 3DF was observed in test animals that were fed the glycated protein diet.

The enzyme inhibitor compounds of the invention block the lysine recovery pathway, preventing formation of toxic 3DG from FL3P.

Described below is a set of extensive criteria that a suitable enzyme inhibitor should display for use in the practice of this invention, as well as certain tests for determining if any putative inhibitor meets these criteria. Candidate kinase inhibitors for use in accordance with this invention may be natural products isolated from plants or microorganisms. Alternatively, they may be synthetic molecules derived from the rational knowledge of the enzymatic reaction and its mechanism. Inhibitors may also be synthesized by combinatorial methods. Combinatorial libraries may be generated from a random starting point. Furthermore, combinatorial methods can be utilized to generate a wide variety of compounds related to previously identified inhibitors of the target FL3P kinase.

Regardless of the source of the putative inhibitor, compounds that do not meet all of the criteria listed below are not considered useful therapeutic agents capable of inhibiting the lysine recovery pathway and thereby preventing, reducing or delaying the onset of diabetic complications or disorders of related etiology.

1. The inhibitor should be a small molecule and readily taken up by cells. In order to meet this criteria, the inhibitor must have a molecular weight of less than 2,000 and more ideally approximately 1,000 daltons or less.

2. The inhibitor must show competitive, noncompetitive, irreversible or suicide inhibition of the FL3P kinase. If the inhibitor is a competitive or noncompetitive inhibitor, the inhibition constant, must be less than about 1 mM. Ideally, it must be less than 100 µM and more ideally, about 40 µM or less. If the inhibitor shows suicide or other irreversible inhibition, this requirement for inhibition constant is rendered moot.

3. The inhibitor must be both soluble in aqueous solution and stable in aqueous solution at physiological pH. The requirement for solubility is met only if the inhibitor, or a salt of the inhibitor, is soluble in physiological saline or serum at a concentration equal to or greater than 10 µM. This stability requirement is met only if a solution of inhibitor dissolved in physiological saline at 37° C. retains greater than 50% of its activity after incubation for one hour. Ideally, the inhibitor must retain greater than 50% activity upon incubation for one day or more.

4. The inhibitor must show acceptable pharmacokinetics. That is, it must remain at a therapeutically effective concentration for at least one hour following administration of the agent. Ideally, it should maintain effective concentration for at least eight hours. More ideally, once per day dosing should be all that is necessary in order to maintain a therapeutic concentration of the inhibitor. This requirement does not mean that the inhibitor must be able to establish a therapeutic concentration after the first dose. Numerous examples of successful pharmaceuticals exist where medical efficacy is seen only upon prolonged dosing. The criterion does mean that, once an efficacious concentration is reached, this concentration should be able to be maintained for greater than one hour following the last administration of medication. A test for therapeutic efficacy is described herein.

5. The inhibitor must be non-toxic. This criteria requires that the inhibitor not demonstrate human toxicity when administered at the therapeutic dose. Ideally, toxicity should not be evident when the inhibitor is present at blood and/or target tissue levels of twice that needed for therapeutic effect. More ideally, there should be no appreciable toxicity at levels 6 or more times the therapeutic range. Diabetic complications can only be prevented by long term inhibitor treatment. Therefore, the requirement for non-toxicity must include both acute toxicity and chronic toxicity that may become evident over extended, long term use. Toxicity of candidate molecules can be readily assessed using well established animal studies. Human toxicity is assessed in stage one clinical trials.

Included among the compounds useful in the practice of this invention are those of the formula:

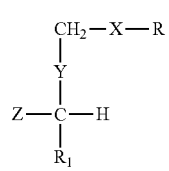

(I)

wherein X is —NR'—, —S(O)—, —S(O)$_2$—, or —O—, R' being selected from the group consisting of H, and linear or branched chain alkyl group ($C_1$-$C_4$) and an unsubstituted or substituted aryl group ($C_6$-$C_{10}$) or aralkyl group ($C_7$-$C_{10}$); R is a substituent selected from the group consisting of H, an amino acid residue, a polyaminoacid residue, a peptide chain, a linear or branched chain aliphatic group ($C_1$-$C_8$), which is unsubstituted or substituted with at least one nitrogen- or oxygen-containing substituent, a linear or branched chain aliphatic group ($C_1$-$C_8$), which is unsubstituted or substituted with at least one nitrogen- or oxygen-containing substituent and interrupted by at least one —O—, —NH—, or —NR"— moiety, R" being linear or branched chain alkyl group ($C_1$-$C_6$) and an unsubstituted or substituted aryl group ($C_6$-$C_{10}$) or aralkyl group ($C_7$-$C_{10}$), with the proviso that when X represents —NR'—, R and R', together with the nitrogen atom to which they are attached, may also represent a substituted or unsubstituted heterocyclic ring having from 5 to 7 ring atoms, with at least one of nitrogen and oxygen being the only heteroatoms in said ring, said aryl group ($C_6$-$C_{10}$) or aralkyl group ($C_7$-$C_{10}$) and said heterocyclic ring substituents being selected from the group consisting of H, alkyl ($C_1$-$C_6$), halogen, $CF_3$, CN, $NO_2$ and —O-alkyl ($C_1$-$C_6$); $R_1$ is a polyol moiety having 1 to 4 linear carbon atoms, Y is a hydroxymethylene moiety —CHOH—; Z is selected from the group consisting of —H, —O-alkyl ($C_1$-$C_6$), -halogen —$CF_3$, —CN, —COOH, and —$SO_3H_2$, and optionally —OH; and the isomers and pharmaceutically acceptable salts of said compound, except that X—R in the above formula does not represent hydroxyl or thiol.

Illustrative examples of nitrogen- or oxygen-containing "R" substituents include those derived from γ-amino-α-hydroxy butyric acid (—$(CH_2)_2$—CHOH—COOH), 1,2,4 triaminobutane (—$(CH_2)_2$—$CHNH_2$—$CH_2NH_3$), 3,6-diamino-5-hydroxyheptanoic acid (—$CH_2$—CH(OH)—$CH_2$—$CH(NH_2)$—$CH_2$—COOH), and the like.

The structure of formula I has asymetric centers and may occur as racemates, racemic mixtures and various stereoisomers, all of such isomeric forms being within the scope of this invention, as well as mixtures thereof.

Although certain of the compounds having the structure of formula I, above, were previously known, others are believed to be novel and as such are within the scope of the present invention, as is the use of all of the compounds of formula I for inhibiting the enzyme-catalyzed production of 3DG in vivo.

Inhibitors of the above formula may be prepared by reacting the appropriate sugar, e.g., glucose, galactose, mannose, ribose, xylose, or the like, with an amino- or hydroxyl-substituted reactant of the type described herein in the presence of an agent, such as $NaBH_3CN$, that selectively reduces the Schiff-base intermediate to an amine, thereby producing an inhibitor having an alcohol moiety (i.e., Y=—CH(—OH)—). The reactive moiety of an amino acid reactant, when used, may be the amine group on the alpha-carbon, or the amine group or hydroxyl group on the acid side chain. Suitable amino acids encompass the essential amino acids. Specific examples include without limitation, glycine, alanine, valine, leucine, isoleucine, serine, threonine, methionine, aspartic acid, phenylalanine, tyrosine, histidine and tryptophan. Other suitable reactants are from the broader class of aminocarboxylic acid, for example, pyroglutamic acid, beta-alanine, gamma-aminobutyric acid, epsilon-amino caproic acid and the like. N-acyl derivatives of the above-mentioned amino acids, such as formyl lysine, may also be used if desired.

Other appropriate reactants include, without limitation, unsubstituted or substituted aryl ($C_6$-$C_{10}$) compounds, wherein the substituent may be alkyl ($C_1$-$C_3$), alkoxy, carboxy, nitro or halogen groups, unsubstituted or substituted alkanes, wherein the substituent may be at least one alkoxy group; or unsubstituted or substituted nitrogen-containing heterocyclic compounds, wherein the substituents may be alkyl ($C_1$-$C_3$), aryl ($C_6$-$C_{10}$), alkoxy, carboxy, nitro or halogen groups. Illustrative examples of the last-mentioned group of reactants include m-methyl-, p-methyl-, m-methoxy-, o-methoxy- and m-nitro-aminobenzenes, o- and p-aminobenzoic acids; n-propylamine, n-butylamine, 3-methoxypropylamine; morpholine and piperidine.

Representative inhibitor compounds having the above formula are set forth in the attached Table A. Examples of known compounds that may be used as inhibitors in practicing this invention include, without limitation, meglumine, sorbitol lysine and mannitol lysine. A preferred inhibitor is 3-O-methyl sorbitollysine.

It appears that the locus of uptake of the inhibitors in vivo is the kidney, as demonstrated by the data in Example 16, below.

TABLE A

| Compound Name | X | R | $R_1$ | Y | Z |
|---|---|---|---|---|---|
| | | a | | | |
| 3-O-methyl sorbitollysine | —N—H | $(CH_2)_4$<br>H—C—$NH_2$<br>COO$^-$ | CHOH<br>CHOH<br>$CH_2OH$ | HC—OH | —O—$CH_3$ |
| galactitol lysine | " | " | " | H—C—OH | —OH |

TABLE A-continued

| Compound Name | X | R | R$_1$ | Y | Z |
|---|---|---|---|---|---|
| 3-deoxy sorbitol lysine | " | " | " | " | —H |
| 3-deoxy-3-fluoro-xylitol lysine | " | " | CHOH<br>\|<br>CH$_2$OH | " | —F |
| 3-deoxy-3-cyano sorbitol lysine | " | " | CHOH<br>\|<br>CHOH<br>\|<br>CH$_2$OH | " | —C≡N |
| 3-deoxy-sedoheptitol spermine$^b$ | —N—CH$_3$<br>\|<br>(CH$_2$)$_3$<br>\|<br>NH<br>\|<br>(CH$_2$)$_4$<br>\|<br>NH<br>\|<br>(CH$_2$)$_3$<br>\|<br>NH$_2$ | | CHOH<br>\|<br>CHOH<br>\|<br>CHOH<br>\|<br>CH$_2$OH | H—C—OH | H | a - lysine residue
b - spermine residue

The inhibitor compounds described herein can form pharmaceutically acceptable salts with various inorganic or organic acids or bases. Suitable bases include, e.g., alkali metal salts, alkaline earth metal salts, ammonium, substituted ammonium and other amine salts. Suitable acids include, e.g., hydrochloric acid, hydrobromic acid and methanesulfonic acid.

The pharmaceutically acceptable salts of the compounds of formula I can be prepared following procedures which are familiar to those skilled in the art.

The ability of a compound to inhibit the FL3P kinase can be determined using a wide variety of kinase activity assays. One useful assay involves incubating the potential inhibitor with fructose-lysine and ATP in the presence of kidney homogenate or other enzyme source.

A solution of the assay components is prepared, which typically contains 1 millimole or less of the inhibitor compound of this invention, an amount of fructose lysine (FL) in the range of 1-10 millimoles, an amount of ATP in the range of 0.1-10 millimoles and an amount of the enzyme source which is sufficient to convert FL to fructose lysine-3-phosphate. The incubation should be conducted within a pH range of 4.5 to 9.5 and ideally at neutral or near neutral pH. The incubation should be carried out at a temperature that is compatible with enzyme activity, between 4° and 40° C. Ideally, the incubation is carried out at physiological temperature. After incubation, the reaction is stopped by acid precipitation of the protein and the production of FL3P measured by $^{31}$P-NMR spectroscopy. FL3P production will be reduced or eliminated in samples containing an inhibitor compound when compared to control samples that are free of inhibitor.

Other assays have utility for the rapid determination of enzyme inhibition. One such assay involves the use of fructose-lysine and γ-labelled $^{32}$P or $^{33}$P-ATP. Since FL3P does not bind to Dow-1 but ATP and most other phosphates do, it is possible to separate the product FL3P from the remaining reaction mixture by passing the assay solution through a column of Dow-1 resin after a predetermined reaction time, typically 10 minutes. The resultant solution is added to a container of scintillation liquid, e.g., Ecoscint A, and counted to determine the amount of radioactivity produced.

As it is difficult to obtain large quantities of human tissue, it is preferable to use a recombinant version of the kinase that is cloned into an expression system, such as *E. coli*. The cloned kinase can be readily obtained from the "shotgun" Cloning of tissue specific cDNA libraries. Such libraries are readily available from commercial sources. For example they may be obtained from Clontech, Palo Alto, Calif. The shotgun cloning envisioned may be performed using the lambda cloning system commercially available from Stratagen, located in San Diego, Calif. This cloning kit contains detailed instructions for its use.

The pharmaceutical preparations of the present invention comprise one or more of the compounds described above, as the active ingredient, in combination with a pharmaceutically acceptable carrier medium or auxiliary agent.

These ingredients may be prepared in various forms for administration, including both liquids and solids. Thus, the preparation may be in the form of tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders; lubricants and the like, as suited to the particular dosage form desired. Representative examples of suitable carrier media include gelatine, lactose, starch, magnesium stearate, talc, vegetable and animal fats and oils, gum, polyalkylene glycol, or the like. *Remington's Pharmaceutical*

Sciences, Fifteenth Edition, E. W. Martin (Mack Publishing Co., Easton, Pa. 1975) discloses various carriers used in formulating pharmaceutical compositions and known techniques for the preparation thereof. Except insofar as any conventional carrier medium is incompatible with the enzyme inhibitors of the invention, such as by producing any undesirable biological effect or otherwise interacting in a deleterious manner with any other component(s) of the pharmaceutical preparation, its use is contemplated to be within the scope of this invention.

In the pharmaceutical preparations of the invention, the active agent(s) may be present in an amount of at least 5% and generally not more than 98% by weight, based on the total weight of the preparation, including carrier medium and/or auxiliary agent(s), if any. Preferably, the proportion of active agent varies between 65%-95% by weight of the composition.

Preferred supplementary active agents are compounds that bind to 3DG in vivo. This class of compounds includes, without limitation, aminoguanidine, amino benzoic acid and derivatives thereof, cysteine and derivatives thereof, amino-substituted imidazoles, 1,2-disubstituted benzimidazoles, substituted 1,2,4-triazoles, diaminopyridine and derivatives thereof, amino-substituted pyrimidines, aminoalcohols, diamines and the like. Anti-hypertensive drugs, including particularly the angiotensin-converting enzyme (ACE) inhibitors, may also be included as supplementary active agents in the pharmaceutical preparations of this invention.

Auxiliary agents, such as compounds that will protect the active compound from acid destruction in the stomach or facilitate the absorption of the active compound into the bloodstream can also be incorporated into the pharmaceutical preparation, if necessary or desirable. Such auxiliary agents may include, for example, complexing agents such as borate or other salts which partially offset the acid conditions in the stomach, and the like. Absorption can be increased by delivering the active compound as the salt of a fatty acid (in those cases where the active compound contains one or more basic functional groups).

The compounds of the invention, along with any supplementary active ingredient(s) may be administered, using any amount and any route of administration effective for inhibiting the FL3P lysine recovery pathway. Thus, the expression "therapeutically effective amount", as used herein, refers to a nontoxic but sufficient amount of the enzyme inhibitor to provide the desired therapy to counteract diabetic complications or to inhibit the metabolic production of 3DG for other medical reasons, such as reducing the effects of aging or other human disease states where AGE-Protein formation has a causative role. The exact amount required may vary, depending on the species, age, and general condition of the patient, the nature of the complications, the particular enzyme inhibitor and its mode of administration, and the like.

The compounds of the invention are preferably formulated in dosage form for ease of administration and uniformity of dosage. Dosage unit form as used herein refers to a physically discrete unit of enzyme inhibitor appropriate for the patient to be treated. Each dosage should contain the quantity of active material calculated to produce the desired therapeutic effect either as such, or in association with the selected pharmaceutical carrier medium. Typically, the compounds of the invention will be administered in dosage units containing from about 1 mg to about 2,500 mg of the compound, by weight of the preparation, with a range of about 5 mg to about 250 mg being preferred.

The compounds of the invention may be administered orally, parenterally, such as by intramuscular injection, intraperitoneal injection, intravenous infusion or the like, depending on the nature of the diabetic complication being treated. The compounds of the invention may be administered orally or parenterally at dosage levels of about 0.7 µg to about 20 mg and preferably from about 30 µg to about 3.5 mg/kg, of patient body weight per day, one or more times a day, to obtain the desired therapeutic effect.

Orally active enzyme inhibitors are particularly preferred, provided the oral dose is capable of generating blood and/or target tissue levels of the inhibitor that are therapeutically active. Those skilled in the art can readily measure the levels of a small molecule inhibitor in deproteinized samples of blood, kidney and other target tissues. The concentration of inhibitor in these samples can be compared with the predetermined inhibitory constant. Tissue levels that are far below the inhibitory constant suggest a lack of therapeutic activity. In the case of irreversible inhibitors, this lack can be confirmed or refuted by assay of the FL3P kinase levels in the respective tissue. In all cases, therapeutic activity can be assessed by feeding the human or animal subject a food rich in glycated lysine residues or fructose-lysine and measuring the amount of 3DG and 3DF in their urine, both before and after feeding. Subjects that have therapeutically active inhibitor in their systems will experience decreased secretion of both 3DG and 3DF and increased urinary secretion of fructose-lysine when compared to levels secreted by these same subjects prior to inhibitor therapy as will be described in further detail hereinbelow.

The compounds of the invention will typically be administered once per day or up to 4-5 times per day, depending upon the exact inhibitor chosen. While a dosing schedule of once-a-day is preferred, diabetic patients are accustomed to paying close attention to their disease state, and so will readily accept more frequent dosing schedules if required, so as to deliver the above-mentioned daily dosage. However, the exact regimen for administration of the compounds and compositions described herein will necessarily be dependent on the needs of the individual patient being treated, the type of treatment administered and the judgment of the attending physician. As used herein, the term "patient" includes both humans and animals.

The inhibitor compounds described herein are useful in counteracting diabetic complications, especially diabetic nephropathy which affects greater than forty percent of diabetics and is the primary cause of end stage renal disease requiring dialysis and transplantation. In addition, these inhibitors may be used for the prevention or treatment of other pathological conditions attributable to the formation of AGE-proteins, such as hypertension, stroke, neurodegenerative disorders, e.g., senile dementia of the Alzheimers type, circulatory disease, glycogen storage diseases including Fanconi's syndrome, atherosclerosis, osteoarthritis, cataracts and the general debilitating effects of aging.

Preliminary experiments have shown that serious adverse health effects result from stimulation of the lysine recovery pathway through long-term consumption of glycated proteins. As was the case with FL, elevation of FL3P, 3DG and 3DF was observed in test animals that were fed a glycated protein diet. See Table B. After eight months of such a diet clear evidence of kidney pathology, resembling that found in diabetic kidneys, was seen in the animals on the glycated protein diet, as described further in Example 10, below. Transient elevation of 3DG and 3DF levels were also observed in the urine of human volunteers who ate a small amount of the glycated protein.

TABLE B

| % Glycated Protein | FL3P conc. (nM-in Kidney) | 3DG/3DF concs (µM-in plasma) |
|---|---|---|
| 0 | 97 | 1.4/0.05 |
| 1 | 295 | — |
| 2.5 | 605 | — |
| 5 | 937 | — |
| 10 | 1066 | 3.6/0.12 |
| 20 | 1259 | 5.2/0.14 |
| 30 | 1267 | 6.2/0.28 |

Since stimulation of the newly discovered lysine recovery pathway leads to substantial increases in systemic 3DG levels, an investigation was carried out to determine whether a glycated diet would cause significant effects on pregnancy. The results obtained so far suggest there is a very strong effect due to this pathway, as will appear in the examples that follow.

Furthermore, it is well known that in susceptible strains of rats and mice the diets on which the animals are maintained in early life (following weaning), can have a marked effect on the incidence of type 1 diabetes, with the incidence ranging from 10% to 90%. Considerable effort has been put into investigating this phenomenon over the last 10 years. See, for example, Diabetes, 46(4): 589-98 (1997) and Diabetes Metab. Rev., 12(4): 341-59 (1996), and references cited therein. An investigation has been undertaken by certain of the present inventors with respect to two diets which are at the extremes for induction of diabetes. AIN-93 (Dyets, Inc.) causes the least incidence of diabetes and produces the lowest ratio of urinary 3DF/creatinine (1.0) yet observed. Purina 500 induces the highest incidence of diabetes and produces a 2.5 fold increase in the 3DF/creatinine ratio. Since FL3P, 3DG and 3DF were observed in the pancreas of rats, it is likely that fructoselysine kinase and the metabolites of this metabolic pathway are involved in the development of Type I diabetes. Animals which are susceptible to this type of diabetes (a useful model of insulin dependent or Type I diabetes in humans) have an abnormal immune system which makes them sensitive to an unknown antigen which develops in the β-cells of the pancreas, resulting in an autoimmune attack by the animal's own immune system on its β-cells. This results in their subsequent destruction, thereby depriving the animal of the ability to make insulin. It is well known that 3DG reacting with proteins can make new antigenic sites. Thus, the source of the antigenic properties of the various diets appears to be the 3DG created by the decomposition of fructoselysine-3-phosphate in the pancreas.

Also, because 3DG is known to interact with amines generally, it may be able to interact with DNA and show mutagenic and carcinogenic potential, as well as crosslink proteins.

The discovery of the FL3P lysine recovery pathway makes it practical, for the first time, to differentiate the diabetic population and to determine which subset of the population is likely to develop to diabetic complications. This determination can be conveniently carried out on a biological fluid of the test subject, such as urine, blood fractions (particularly plasma or serum), lymph fluid, interstitial fluid or the like.

After an overnight fast, a human subject is fed a food source containing a relatively high concentration of glycated-lysine residues. By way of example, this food can be in the form of a casein/sugar "cookie", such as described in Example 5, below, or some other suitable source of glycated-lysines or synthetic fructose-lysine. When proteins containing glycated-lysine residues are utilized, the content of glycated-lysine should be preferably between 0.02 and 10% of total protein amino acid, or more preferably between about 0.2 and 0.4%. The total amount of glycated-lysine residues in the oral dose should be about 0.3 grams. Preferably, a urine sample is collected before consumption of the glycated-lysine source, then at one, three and five hours, or such other appropriate times as may be warranted by the individual clinical situation.

The 3DG and 3DF levels in these urine samples are measured and the ratios of these metabolites calculated. The particular methodology utilized in this measurement is not essential to the practice of this invention. The GC method described in Example 5, below, may be utilized, if desired. Alternatively, colorimetric or immunological assay methods can be used, as will be apparent to those skilled in the art.

It is clear that the major risk factor faced by diabetics is glycemic control, as was clearly demonstrated by the recently completed Diabetes Control and Complications Trial. However, the incidence of diabetic complications cannot be explained solely by blood sugar levels; a fairly wide scatter is seen when the incidence of diabetic complications is compared to historical blood sugar levels.

One method for determining that subset of the diabetic population which is most at risk for developing diabetic complications is a particularly significant aspect of the present invention. This method involves the measurement of FL, 3DG and 3DF levels before and, optimally, after ingesting a source of glycated lysine.

For example, normal subjects have a fasted 3DG to 3DF ratio in urine of about 0.025, whereas diabetics have higher ratios, which may be up to five fold higher, or more. This is borne out by the data in FIG. 7, which shows that normoglycemics have a 3DG/3DF ratio of 0.025 (1/39.77) with quite tight scatter around this value, whereas diabetics have a more than 2 fold higher average ratio (average 0.069) with much more scatter around the average.

As demonstrated herein, diabetics have increased production of 3DG. Therefore, resistance to diabetic complications requires highly efficient removal of this toxic metabolite. The ratio of 3DG to 3DF, calculated by the method described herein, allows one to assess the efficiency of the 3DG detoxification pathways. Those individuals with low ratio will be generally resistant to developing diabetic complications. Individuals with higher ratios, including ratios contained within the normal range, are more at risk, while individuals with elevated ratios above the normal range are particularly at risk for developing these complications.

Recent measurements of fructoselysine (FL) in the plasma and urine of four different rat strains have demonstrated considerable variability in the manner in which their respective kidneys process FL in blood. In two of the four strains (Long Evans, Brown Norway) virtually all of the FL filtered by the kidney appeared in the urine based upon ratios of this compound and its metabolites with creatinine. With the other two strains (Sprague Dawley, Fischer) 10-20% of the FL in the plasma appeared in the urine, based on comparisons with creatinine filtration. These measurements strongly suggest a major variability in FL processing in the mammalian kidney. Given what is known about the functional equivalence of rodent and human kidneys, it is reasonable to assume a similar variation in FL processing will exist among humans. Since FL is the primary input to the fructoselysine recovery pathway, the entire pathway is likely to be substantially stimulated in those humans in whom a large amount of FL is absorbed from the ultrafiltrate, leading to the high local levels of 3-deoxyglucosone (3DG) in the kidney, as well as systemically throughout the body. This observation may serve as the basis of a diagnostic test in which the comparison of a sample of plasma or serum contemporaneously obtained with a urine sample would determine the flux of FL into the kidney, and the fraction of that flux which appears in the urine. Those individuals in whom this ratio is substantially lower than one (1) would then be at risk for developing a variety of kidney pathologies including, but not limited to, diabetic nephropathy, kidney failure in old age and kidney carcinoma.

Therapeutic efficacy of the kinase inhibitors of the invention can be easily and safely determined using a test of the lysine recovery pathway. The test protocol is identical to the one presented immediately above, with the exception that urinary fructoselysine levels are measured in addition to urinary 3DG and 3DF levels. It is useful to conduct this test both before and after initiating FL3P kinase inhibitor therapy. The urine levels of 3DG and 3DF are summed at each time point and compared to the levels of fructose-lysine measured in the same sample.

The peak levels of 3DG and 3DF found in urine following ingestion of food rich in glycated-lysine residues are derived from the activity of the lysine recovery pathway. The ratio of the concentration of these metabolites to unreacted fructose-lysine (which is a normal component of human urine) reflects the activity of this pathway. Inhibition of the lysine recovery pathway will cause a decrease in the amount of 3DG and 3DF excreted, and an increase in the excreted levels of fructose-lysine. Thus, therapeutic efficacy of a kinase inhibitor can be quantitated by measuring the decrease of the (3DG+3DF)/fructose-lysine ratio following initiation of therapy. It is noteworthy that urine volume or metabolite concentrations are not a factor in interpreting this assay, as only a ratio of metabolites is considered.

It will be appreciated from the foregoing disclosure that orally digested food containing high concentrations of glycated-lysine residues will lead to the production of kidney and serum 3DG. It is reasonable to caution individuals at risk for kidney disease, for example diabetics, to avoid food with these high concentrations. Concentrations of glycated-lysine residues can be measured using a wide variety of methods. One such measurement method is described in Example 4, below. However, any suitable measurement methodology that accurately determines the levels of glycated-lysine residues can be substituted in place of the assay method exemplified below. Examples of assay methods specifically contemplated include but are not limited to colorimetric and immunological methods.

Regardless of the method of measurement employed, it is within the scope of the present invention to determine the content of glycated-lysine residues in prepared foods and to apprise individuals at risk for developing kidney dysfunction of these determinations, so that such individuals may refrain from ingesting foods high in glycated-lysine content.

The following examples are provided to describe the invention in further detail. These examples are provided for illustrative purposes only, and should in no way be construed as limiting the invention. All temperatures given in the examples are in degrees centigrade unless otherwise indicated.

EXAMPLE 1

Isolation and Identification of FL3P

A $^{31}$P NMR analysis of a perchloric acid extract of diabetic rat kidneys showed a new sugar monophosphate resonance at 6.24 ppm which is not observed in non-kidney tissue and is present at greatly reduced levels in non-diabetic kidney. The compound responsible for the observed resonance was isolated by chromatography of the extract on a microcrytalline cellulose column using 1-butanol-acetic acid-water (5:2:3) as eluent. The structure was determined by proton 2D COSY to be fructose-lysine 3-phosphate. This was later confirmed by injecting animals with FL, prepared as previously described (Finot and Mauson, Helv. Chim. Acta, 52: 1488 (1969)), and showing direct phosphorylation to FL3P. Using FL specifically deuterated in position-3 confirmed the position of the phosphate at carbon-3. This was performed by analyzing the $^{31}$P NMR spectra both coupled and decoupled. The normal P—O—C—H coupling produces a doublet in FL3P with a J value of 10.3 Hz, whereas P—O—C-D has no coupling and produces a singlet both coupled and decoupled, as was found for 3-deuterated FL3P. A unique property of FL3P is that when treated with sodium borohydride it is converted into two new resonances at 5.85 and 5.95 ppm, which correspond to mannitol and sorbitol-lysine 3-phosphates.

EXAMPLE 2

Synthesis of FL3P 1 mmol of dibenzyl-glucose 3-phosphate and 0.25 mmol of α-carbobenzoxy-lysine was refluxed in 50 ml of MeOH for 0.3 hours. The solution was diluted with 100 ml water and chromatographed on a Dow-50 column (2.5×20 cm) in the pyridinium form and eluted first with water (200 ml) and then with 600 ml buffer (0.1M pyridine and 0.3M acetic acid). The target compound eluted at the end of the water wash and the beginning of the buffer wash. Removal of the cbz and benzyl blocking groups with 5% Pd/C at 20 psi of hydrogen gave FL3P in 6% yield.

EXAMPLE 3

Enzymatic Production of FL3P From FL and ATP and Assay for Screening Inhibitors

Initially $^{31}$P NMR was used to demonstrate kinase activity in the kidney cortex. A 3 g. sample of fresh pig kidney cortex was homogenized in 9 ml. of 50 mM Tris.HCl containing 150 mM KCl, 5 mM DTT, 15 mM $MgCl_2$, pH 7.5. This was centrifuged at 10,000 g for 30 minutes, and then the supernate centrifuged at 100,000 g for 60 minutes. Ammonium sulfate was added to 60% saturation. After 1 hour at 4° the precipitate was collected by centrifugation and dissolved in 5 ml. of original buffer. A 2 ml aliquot of this solution was incubated with 10 mM ATP and 10 mM of FL (prepared as in Example 1, above) for 2 hours at 37°. The reaction was quenched with 300 uL of perchloric acid, centrifuged to remove protein, and desalted on a column of Sephadex G 10 (5×10 cm). $^{31}$P NMR analysis of the reaction mixture detected formation of FL3P.

Based on the proof of kinase activity thus obtained, a radioactive assay was developed. This assay was designed to take advantage of the lack of binding to Dow-1 anion exchange resin by FL3P. This characteristic of FL3P was discovered during efforts to isolate it. Since most phosphates bind to this resin, it was suspected that the bulk of all compounds that react with ATP as well as any excess ATP would be bound, leaving FL3P in solution. The first step was to determine the amount of resin required to remove the ATP in the assay. This was accomplished by pipetting the mixture into a suspension of 200 mg. of Dow-1 in 0.9 ml $H_2O$, vortexing and centrifuging to pack the resin. From this 0.8 ml. of supernate was pipetted onto 200 mg. of fresh dry resin, vortexed and centrifuged. A 0.5 ml volume of supernate was pipetted into 10 ml of Ecoscint A and counted. Residual counts were 85 cpm. This procedure was used for the assay.

The precipitate from 60% ammonium sulfate precipitation of the crude cortex homogenate was redissolved in the homogenate buffer at 4°. The assay contains 10 mM $\gamma^{33}$P-ATP (40,000 cpm), 10 mM FL, 150 mM KCl, 15 mM $MgCl_2$, 5 mM DTT in 0.1 ml of 50 mM Tris.HCl, pH 7.5. The relationship between rates of FL3P production and enzyme concentration was determined using triplicate determinations with 1, 2 and 4 mg of protein for 30 minutes at 37°. Blanks run concurrently without FL were subtracted and the data recorded. The observed activity corresponds to an approximate FL3P synthesis rate of 20 nmols/hr./mg. protein.

EXAMPLE 4

Inhibition of the Formation of 3-Deoxyglucosone by Meglumine and Various Polyollysines a. General Polyollysine Synthesis.

The sugar (11 mmoles), α-carbobenzoxy-lysine (10 mmols) and $NaBH_3CN$ (15 mmoles) were dissolved in 50 ml of MeOH—$H_2O$ (3:2) and stirred at 25° for 18 hours. The solution was treated with an excess of Dow-50 (H) ion exchange resin to decompose excess $NaBH_3CN$. This mixture (liquid plus resin) was transferred onto a Dow-50 (H) column (2.5×15 cm) and washed well with water to remove excess sugar and boric acid. The carbobenzoxy-polyollysine was eluted with 5% $NH_4$ OH. The residue obtained upon evaporation was dissolved in water-methanol (9:1) and reduced with hydrogen gas (20 psi) using a 10% palladium on charcoal catalyst. Filtration and evaporation yields the polyollysine.

b. Experimental Protocol for Reduction of Urinary and Plasma 3-Deoxyglucosone by Sorbitollysine, Mannitollysine and Galactitollysine.

Urine was collected from six rats for three hours. A plasma sample was also obtained. The animals were then given 10 μmols of either sorbitollysine, mannitollysine, or galactitollysine by intraperitoneal injection. Urine was collected for another three hours, and a plasma sample obtained at the end of the three hours.

3-deoxyglucosone was measured in these samples, as described in Example 5, below, and variable volumes were normalized to creatinine. The average reduction of urinary 3-deoxyglucosone was 50% by sorbitollysine, 35% by mannitollysine and 35% by galactitollysine. Plasma 3-deoxyglucosone was reduced 40% by sorbitollysine, 58% by mannitolysine and 50% by galactitollysine.

c. Use of meglumine to reduce urinary 3-deoxyglucosone. Three rats were treated as in b), immediately above, except meglumine (100 μmols) was injected intraperitoneally instead of the above-mentioned lysine derivatives. Three hours after the injection the average 3-deoxyglucosone concentrations in the urine were decreased 42%.

EXAMPLE 5

Elevation of Urinary FL, 3DG and 3DF in Humans Following Ingestion of Glycated Protein a. Preparation of glycated protein containing food product: 260 g. of casein, 120 g. of glucose and 720 ml. of water were mixed to give a homogeneous mixture. This mixture was transferred to a metal plate and cooked at 65° for 68 hours. The resulting cake was then pulverized to a coarse powder. This powder contained 60% protein as determined by the Kjeldahl procedure.

b. Measurement of glycated lysine content: 1 g of the powder prepared as in step a., above, was hydrolyzed by refluxing with 6N HCl for 20 hours. The resulting solution was adjusted to pH 1.8 with NaOH solution and diluted to 100 ml. The fructoselysine content was measured on an amino acid analyzer as furosine, the product obtained from acid hydrolysis of fructoselysine. In this way, it was determined that the cake contained 5.5% (w/w) fructoselysine.

c. Experimental protocol: Volunteers spent two days on a fructoselysine-free diet and then consumed 22.5 g of the food product prepared as described herein, thus effectively receiving a 2 g. dose of fructoselysine. Urine was collected at 2 hour intervals for 14 hours and a final collection was made at 24 hours.

d. Measurement of FL, 3DG and 3DF in urine: FL was measured by HPLC with a Waters 996 diode Array using a Waters C18 Free Amino Acid column at 46° and a gradient elution system of acetonitrile-methyl alcohol-water (45:15:40) into acetonitrile-sodium acetate-water (6:2:92) at 1 ml./min. Quantitation employed an internal standard of meglumine.

3DF was measured by HPLC after deionization of the sample. Analyses were performed on a Dionex DX-500 HPLC system employing a PA1 column (Dionex) and eluting with 32 mM sodium hydroxide at 1 ml./min. Quantitation was performed from standard curves obtained daily with synthetic 3DF.

3DG was measured by GC-MS after deionization of the sample. 3DG was derivatized with a 10-fold excess of diaminonaphthalene in PBS. Ethyl acetate extraction gave a salt free fraction which was converted to the trimethyl silyl ethers with Tri-Sil (Pierce). Analysis was performed on a Hewlett-Packard 5890 selected ion monitoring GC-MS system. GC was performed on a fused silica capillary column (DB-5, 25 mx. 25 mm) using the following temperature program: injector port 250°, initial column temperature 150° which is held for 1 minute, then increased to 290° at 16°/minute and held for 15 minutes. Quantitation of 3DG employed selected ion monitoring using an internal standard of U-13C-3DG.

Figure 3:
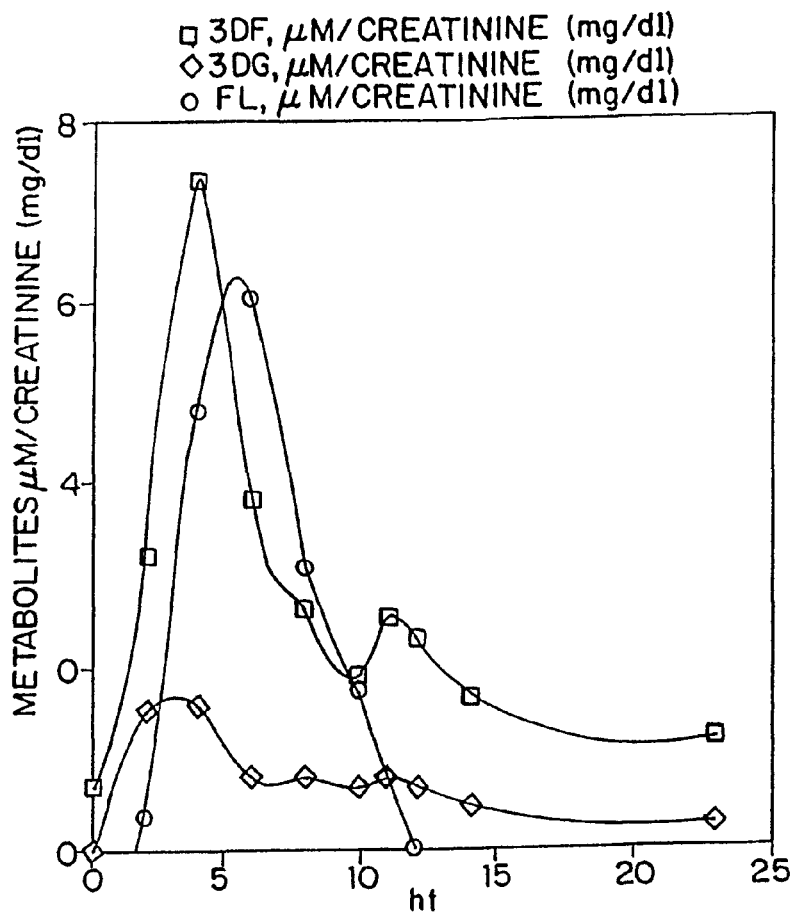
FIG. 3 is a graphical representation of a urinary profile showing the variation over time of 3DF, 3DG and FL from a single individual fed 2 g. of FL and followed for 24 hours.

The graph shown in FIG. 3 represents production of FL, 3DF and 3DG in the urine of one volunteer after consuming the glycated protein. The rapid appearance of all three metabolites is clearly evident. Both 3DF and 3DG show a slight elevation even after twenty-four hours.

Figure 4:
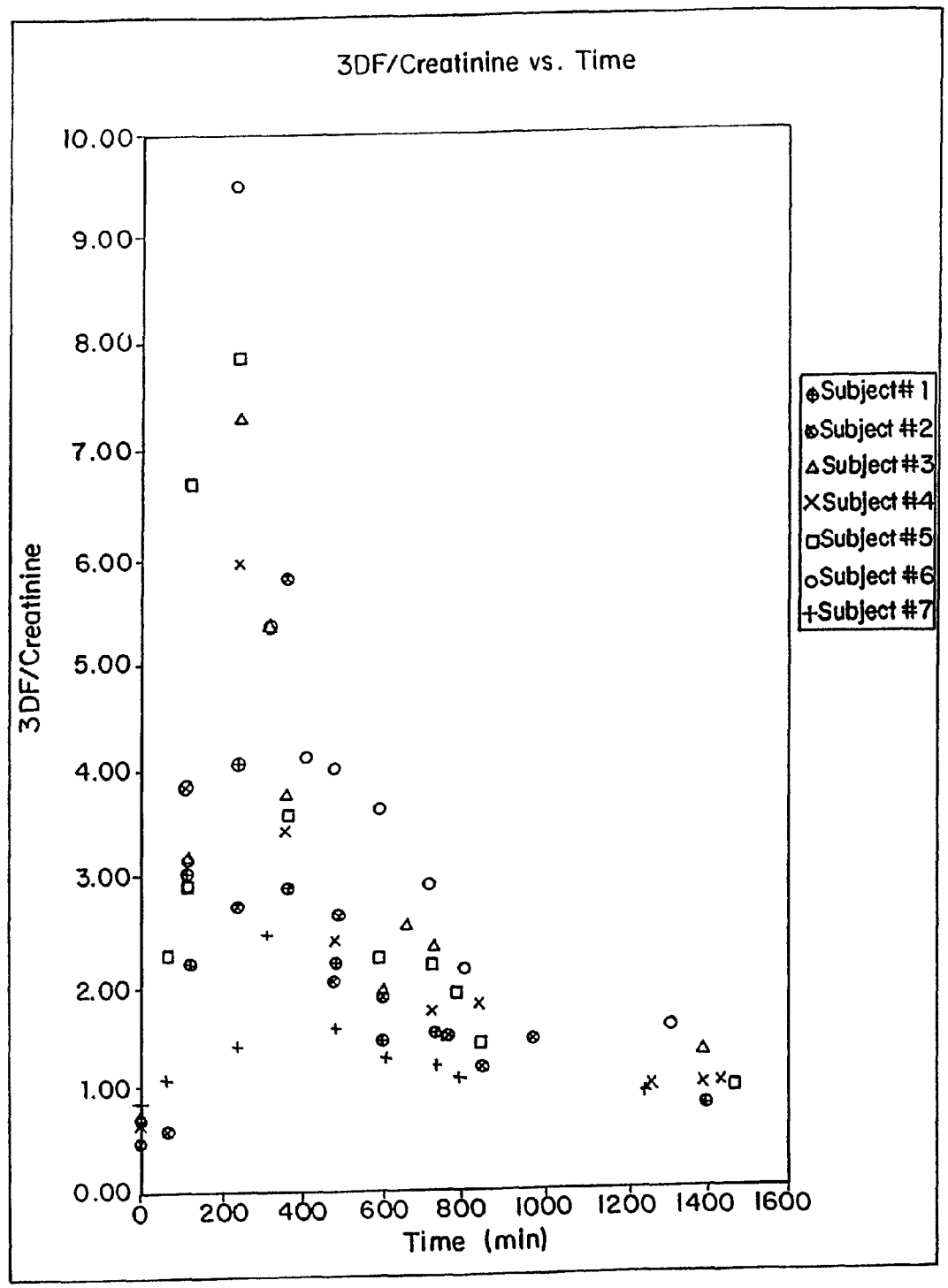
FIG. 4 is a graphical representation of urinary excretion over time of 3DF from seven volunteers fed 2 g. of fructoselysine.

The graph shown in FIG. 4 represents the formation of 3DF in each of the members of a seven person test group. A similar pattern was seen in all cases. As appears in FIG. 4, 3DF excretion peaks about 4 hours after the FL bolus and a slight elevation of 3DF is noticeable even 24 h after the bolus.

EXAMPLE 6

Feeding Experiment

N-acetyl-β-glucosaminidase (NAGase) is an enzyme excreted into the urine in elevated concentration in diabetics. It is thought to be an early marker of tubular damage, but the pathogenesis of increased NAGase in urine is not well understood. The increased urinary output of NAGase in diabetics has been proposed to be due to activation of lysosomes in proximal tubules induced by diabetes with an increased output into the urine rather than destruction of cells.

Figure 5:
FIG. 5 shows a graphical comparison of 3DF and N-acetyl-β-glucosaminidase (NAG) between a group of control animals and an experimental group maintained on a feed containing 0.3% glycated protein.
Figure 6:
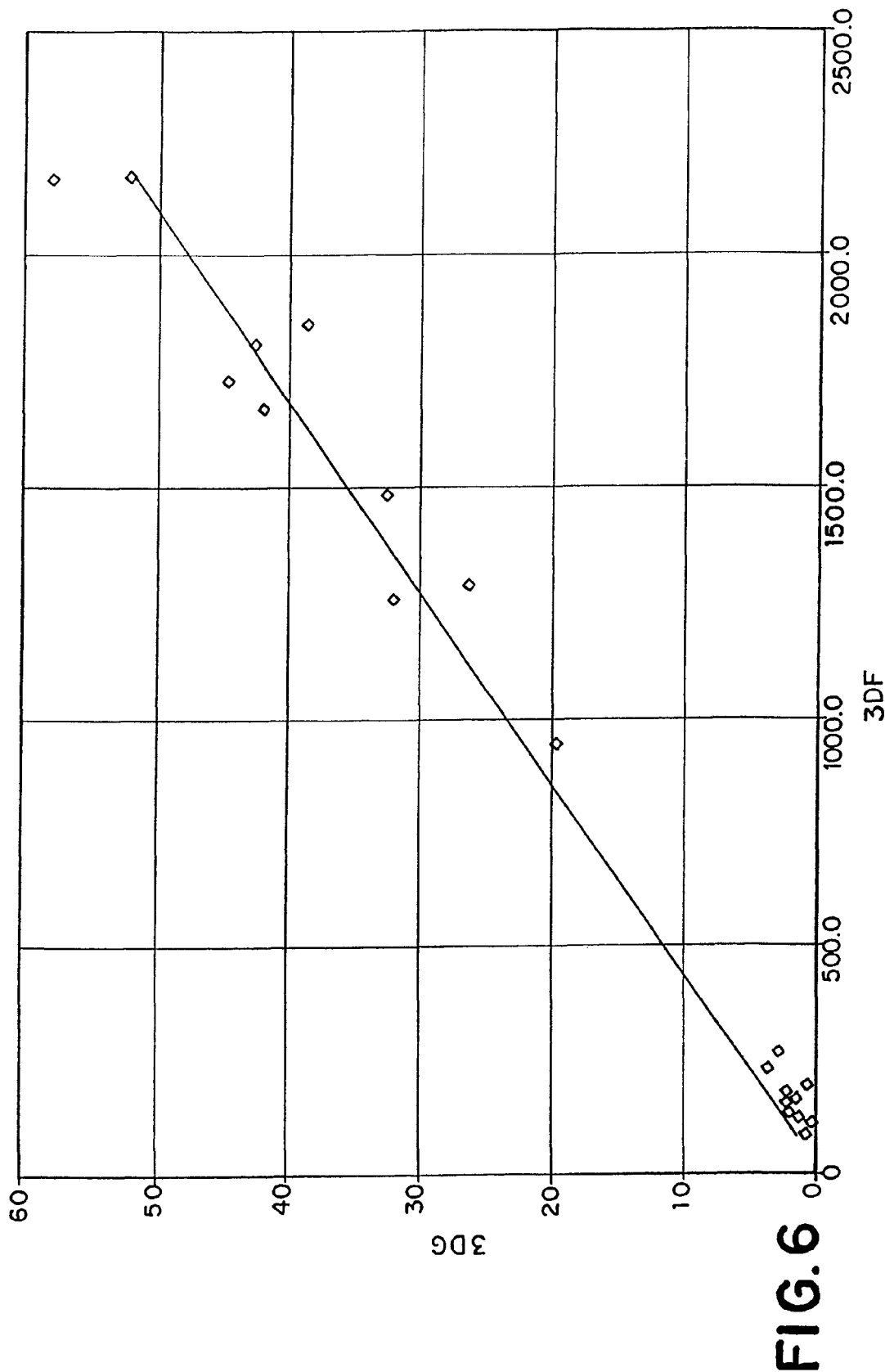
FIG. 6 is a graph showing the linear relationship between 3DF and 3DG levels in urine of rats fed either a control diet or one enriched in glycated protein.

The results obtained in this example show that in all comparisons 3DF and NAGase levels are elevated in the experimental group relative to the control. Thus, animals fed glycated protein excrete excess NAGase into their urine, similar to results obtained with diabetics. There is an approximate 50% increase in NAGase output compared with control animals. These animals also have a five-fold increase in urine 3DF compared with controls. Urinary 3DF correlates extremely well with 3DG, as can be seen in FIGS. 5 and 6. Both compounds appear to be removed from the plasma at the glomerular filtration rate, with no reabsorption.

EXAMPLE 7

SDS Gel of Kidney Proteins

Two rats were injected daily with 5 µmols. of either FL or mannitol (used as a control) for 5 days. The animals were sacrificed and the kidneys removed and dissected into the cortex and medulla. Tissues were homogenized in 5 volumes of 50 mM Tris.HCl containing 150 mM KCl, 15 mM $MgCl_2$ and 5 mM DTT, pH 7.5. Cellular debris was removed by centrifugation at 10,000 g for 15 minutes, and the supernate was then centrifuged at 150,000 g for 70 minutes. The soluble proteins were analyzed by SDS PAGE on 12% polyacrylamide gels as well as on 4-15 and 10-20% gradient gels. In all cases, lower molecular weight bands were missing or visually reduced from the kidney extract of the animal injected with FL when compared with the animal injected with mannitol.

EXAMPLE 8

Synthesis of 3-O-Methylfructose Lysine

A suspension of 19.4 g (0.1 mol) of anhydrous 3-O-methyl glucose and 1 g of sodium bisulfite in 30 ml of methanol and 15 ml of glycerol was refluxed for 30 minutes, followed by the addition of 0.035 mol of α-carbobenzoxy-lysine and 4 ml of acetic acid. This solution was refluxed for 3 hours. The solution was treated with 1 volume of water and chromatographed on a Dowex-50 column (4×50 cm) in the pyridinium form, and eluted first with water and then with pyridinium acetate. Fractions containing the pure material were combined and evaporated. The resulting material was dissolved in 50 ml of water-methanol (9:1) and reduced with hydrogen gas (20 psi) using a 10% palladium on charcoal catalyst. Filtration and evaporation gave 3-O-methyl-fructoselysine.

Other specific compounds having the structure of formula (I), above, may be made e.g. by glycation of a selected nitrogen- or oxygen-containing starting material, which maybe an amino acid, polyaminoacid, peptide or the like, with a glycating agent, such as fructose, which may be chemically modified, if desired, according to procedures well know to those skilled in the art.

EXAMPLE 9

Additional Assay for FL3P Kinase Activity a. Preparation of Stock Solutions:
An assay buffer solution was prepared which was 100 mM HEPES pH 8.0, 10 mM ATP, 2 mM $MgCl_2$, 5 mM DTT, 0.5 mM PMSF. A fructosyl-spermine stock solution was prepared which was 2 mM fructosyl-spermine Hcl. A spermine control solution was prepared which was 2 mM spermine Hcl.
b. Synthesis of Fructosyl-spermine:
Synthesis of fructosyl-spermine was performed by an adaptation of a known procedure (J. Hodge and B. Fisher, Methods Carbohydr. Chem., 2: 99-107 (1963)).

A mixture of spermine (500 mg), glucose (500 mg) and sodium pyrosulfite (80 mg) was prepared in a molar ratio of 8:4:1 (spermine:glucose:pyrosulfite) in 50 ml of methanol-water (1:1) and refluxed for 12 hours. The product was diluted to 200 ml with water and loaded onto a DOW-50 column (5×90 cm). The unreacted glucose was removed by 2 column volumes of water and the product and unreacted spermine were removed with 0.1 M $NH_4OH$. Pooled peak fractions of the product were lyophilized and concentration of fructosyl-spermine was determined by measuring the integral of the C-2 fructosyl peak in a quantitative $^{13}C$ NMR spectrum of the product (NMR data collected with a 45° pulse, a 10 second relaxation delay and without NOE decoupling).

c. Assay of Kinase for Purification:
An incubation mixture was prepared including 10 µl of the enzyme preparation, 10 µl of assay buffer, 1.0 µCi of $^{33}P$ ATP, 10 µl of fructosyl-spermine stock solution and 70 µl of water and incubated at 37° C. for 1 hour. At the end of the incubation 90 µl (2×45 µl) of the sample is spotted onto two 2.5 cm diameter cellulose phosphate disks (Whatman P-81) and allowed to dry. The disks were washed extensively with water. After drying, the disks were placed in scintillation vials and counted.

Each enzyme fraction was assayed in duplicate with an appropriate spermine control.

EXAMPLE 10

Kidney Pathology Observed in Test Animals on Glycated Protein Diet

Three rats were maintained on a glycated protein diet (20% total protein; 3% glycated) for 8 months and compared to 9 rats of the same age maintained on a control diet. The primary finding was a substantial increase in damaged glomeruli in the animals on the glycated diet. Typical lesions observed in these animals were segmental sclerosis of the glomerular tuft with adhesion to Bowman's capsule, tubular metaplasia of the parietal epithelium and intestitial fibrosis. All three of the animals on the glycated protein diet, and only one of the animals on the control diet showed more than 13% damaged glomeruli. The probability of this happening by chance is less than 2%. In addition to the pathology observed in the glomeruli, a number of hylinated casts within tubules were observed. More of these were found in animals on the glycated diet, although these were not quantitated. Increased levels of NAGase were also observed in the animals on the glycated diet.

From the results of this experiment, the glycated diet appeared to cause the test animals to develop a series of histological lesions similar to those seen in the diabetic kidney.

EXAMPLE 11

Effects of Glycated Diets on Pregnancy

In a preliminary experiment, 5 mice pairs were placed on a glycated diet (18% total protein; 3% glycated) and bred six times over a period of 7 months. The resulting six pregnancies produced the following live pups; 17, 23, 13, 0, 3 and 0. In view of this sharp drop in live pups after the third breeding, two cohorts of ten pairs each were put on either a glycated diet (13% total protein; 3% glycated) or a control diet (13% total protein; 0% glycated). Thus far, the two groups of pups have been bred four times obtaining similar results in both groups. The first pregnancy produced 49/20 (glycated/control) pups; the second, 18/41; the third 37/27; and the fourth 20/33. The fifth pregnancy is currently underway. The mice pairs have been tested for hyperglycemia. The blood glucose levels are 120 and 112 mg/dl in the experimental and control groups, respectively.

Preliminary measurements of the 3DF levels in the mice urine indicate, as expected, a substantial elevation (approximately 5-10 fold) of the systemic 3DF when on the glycated diet described herein.

EXAMPLE 12

Carcinogenic Effects of Fructoselysine Pathway

To investigate the carcinogenic potential of metabolites formed in the fructoselysine pathway, experiments have been conducted on a strain of rats with a high susceptibility to kidney carcinomas. Four rats were put on a glycated protein diet and three rats on a control diet. After ten weeks on the diet, the animals were sacrificed and their kidneys examined. In all four animals on the diet, kidney carcinomas of size greater than 1 mm were found, whereas no lesions this large were found in the control animals. The probability of this happening by chance is less than 2%. The data show that the elevated 3DG levels caused by the excess fructoselysine coming from the glycated protein in the animals diet found in the kidney tubular cells (known to be the cell of origin of most kidney carcinomas) can interact with the cellular DNA leading to a variety of mutogenic and ultimately carcinogenic events. The possibility exists that this process is important in the development of human cancers in the kidney and elsewhere.

EXAMPLE 13

Dietary Effects of Glycated Protein Diet on Renal Cell Carcinoma in Susceptible Rats In addition experiments assessing the relationship between a glycated protein diet and renal cell carcinoma, twenty-eight rats with a mutation making them susceptible to the development of kidney carcinoma were divided into two cohorts. One cohort was fed a glycated protein diet: the other cohort was on a control diet. The glycated protein diet consisted of a standard nutritious diet to which 3% glycated protein had been added. The glycated protein was made by mixing together casein and glucose (2:1), adding water (2× the weight of the dried material), and baking the mixture at 60° for 72 hours. The control was prepared in the same way except that no water was used and the casein and glucose were not mixed prior to baking. Rats were placed on the diets immediately following weaning at three weeks of age and maintained on the diets ad libitum for the next 16 weeks. The animals were then sacrificed, the kidneys fixed and hemotoxylin and eosin sections were made. These were examined for lesions by a trained pathologist. Four types of lesions were identified. These included: cysts, very small collections of tumor-like cells, typically less than 10 cells; small tumors, 0.5 mm or less, and tumors greater than 0.5 mm. For every type, more lesions were observed in the animals on the glycated diet than on the control diet as shown in the following table.

|  | CYSTS | ≦10 CELLS | ≦0.5 mm | >0.5 mm | TOTAL |
| --- | --- | --- | --- | --- | --- |
| CONTROL | 2 | 9 | 9 | 3 | 23 |
| GLYCATED | 9 | 21 | 32 | 6 | 68 |

To summarize the results, the average number of lesions per kidney section was computed for each diet. These were 0.82±0.74 and 2.43±2.33 in the control and glycated diet, respectively. The likelihood of this happening by chance is about 2 in 100,000.

These results provide strong support for the premise that the effects of the lysine recovery pathway, the discovery of which underlies the present invention, extend to causing mutations, and thus produce a carcinogenic effect as well. These results provide a basis for the development of therapeutic methods and agents to inhibit this pathway in order to reduce cancer in the kidney as well as in other organs where this pathway may have similar effects.

EXAMPLE 14

Urinary Excretion of 3-Deoxy-Fructose is Indicative of Progression to Microalbuminuria in Patients with Type I Diabetes As set forth hereinabove, serum levels of the glycation intermediate, three deoxy-glucosone (3DG) and its reductive detoxification product, three deoxy-fructose (3DF), are elevated in diabetes. The relationship between baseline levels of these compounds and subsequent progression of microalbuminura (MA) has been examined in a group of 39 individuals from a prospective cohort of patients at the Joslin Diabetes Center with insulin-dependent diabetes mellitus (IDDM) and microalbuminuria (based on multiple measurements during the two years of baseline starting between 1990-1993) and not on ACE inhibitors.

Baseline levels of 3DF and 3DG in random spot urines were measured by HPLC and GC-MS. Individuals that progressed to either a higher level of MA or proteinuria in the next four years (n=24) had significantly higher baseline levels of log3DF/urinary creatinine ratios compared to non-progressors (n=15) (p=0.02). Baseline levels determined in this study were approximately 0.24 μmole/mg of creatinine in the progressors vs. approximately 0.18 μmole/mg of creatinine ratios in the non-progressors. Baseline 3DG/urine creatinine ratios did not differ between the groups. Adjustment of the baseline level of HgA$_{Ic}$ (the major fraction of glycoslyated hemoglobin) did not substantially alter these findings. These results provide additional evidence of the association between urinary 3DF and progression of kidney complications on diabetes.

A. Quantification of 3-deoxyfructose

Samples were processed by passing a 0.3 mL aliquot of the test sample through an ion-exchange column containing 0.15 mL of AG 1-X8 and 0.15 mL of AG 50W-X8 resins. The columns were then washed twice with 0.3 mL deionized water, aspirated to remove free liquid and filtered through a 0.45 mm Millipore filter.

Injections (50 μL) of the treated samples were analyzed using a Dionex DX 500 chromatography system. A carbopac PA1 anion-exchange column was employed with an eluant consisting of 16% sodium hydroxide (200 mM) and 84% deionized water. 3DF was detected electrochemically using a pulsed amperometric detector. Standard 3DF solutions spanning the anticipated 3DF concentrations were run both before and after each unknown sample.

B. Measurement of Urine Creatinine

Urine creatinine concentrations were determined by the end-point colormetric method (Sigma Diagnostic kit 555-A) modified for use with a plate reader. Creatinine concentrations were assessed to normalize urine volumes for measuring metabolite levels present therein.

C. Measurement of Albumin in the Urine

To assess albumin levels in the urine of the test subjects, spot urines were collected and immunoephelometry performed on a BN 100 apparatus with the N-albumin kit (Behring). Anti-albumin antibodies are commercially available. Albumin levels in urine may be assessed by any suitable assay including but not limited to ELISA assays, radioimmunoassays, Western and dot blotting.

Based on the data obtained in the study of the Joslin Diabetes Center patients, it appears that elevated levels of urinary 3DF are associated with progression to microalbuminuria in diabetes. This observation provides a new diagnostic parameter for assessing the likelihood of progression to serious kidney complications in patients afflicted with diabetes.

EXAMPLE 15

3-O-Methyl Sorbitollysine Lowers Systemic Levels of 3DG in Normal and Diabetic Rats A cohort of twelve diabetic rats was divided into two groups of six. The first group received saline-only injections, and the second received injections of 3-O-methyl sorbitollysine in saline solution. The same procedure was conducted on a cohort of twelve non-diabetic rats. As summarized in Table C, within one week, the 3-O-methyl sorbitollysine treatment significantly reduced the plasma 3DG levels as compared to the respective saline controls in both diabetic and non-diabetic rats.

TABLE C

3-O-Methyl sorbitollysine reduces plasma 3DG levels in diabetic and non-diabetic rats.

|  | Diabetic Rats Plasma, Day 8 | Non-diabetic Rats Plasma, Day 8 |
|---|---|---|
| Control (n = 6) | 0.94 ± 0.28 µM | 0.23 ± 0.07 µM |
| 3-O-methyl Sorbitollysine (n = 6) | 0.44 ± 0.10 µM | 0.13 ± 0.02 µM |
| Percent reduction | 53% | 43% |
| t-test | P = 0.0006 | P = 0.0024 |

The ability of 3-O-methyl sorbitollysine to reduce systemic 3DG levels suggests that diabetic complications other than nephropathy (e.g., retinopathy and stiffening of the aorta) may also be controllable by Amadorase inhibitor therapy.

EXAMPLE 16

Locus of 3-O-Methyl Sorbitollysine Uptake In Vivo is the Kidney

Six rats were injected intraperitoneally with 13.5 mmoles (4.4 mg) of 3-O-methyl sorbitollysine. The rats' urine was collected for 3 hours, after which the rats were sacrificed. The tissues to be analyzed were removed and freeze clamped in liquid nitrogen. Perchloric acid extracts of the tissues were used for metabolite analysis. The tissues examined were taken from the brain, heart, muscle, sciatic nerve, spleen, pancreas, liver and kidney. Plasma and urine were also analyzed.

The only tissue extract found to contain 3-O-methyl sorbitollysine was that of the kidney. The urine also contained 3-O-methyl sorbitollysine, but plasma did not. The percentage of the injected dose recovered from urine and kidney varied between 39 and 96%, as shown in Table D, below.

TABLE D

| Rat # | nmols 3OMeSL* Injected | nmols 3OMeSL in urine | nmols 3OMeSL in kidneys | total 3OMeSL recovered | % 3OMeSL recovered |
|---|---|---|---|---|---|
| 2084 | 13500 | 2940 | 10071 | 13011 | 96.4 |
| 2085 | 13500 | 1675 | 6582 | 8257 | 61.2 |
| 2086 | 13500 | 1778 | 5373 | 7151 | 53.0 |
| 2087 | 13500 | 2360 | 4833 | 7193 | 53.3 |
| 2088 | 13500 | 4200 | 8155 | 12355 | 91.5 |
| 2089 | 13500 | 1355 | 3880 | 5235 | 38.8 |

*3-O-methyl sorbitollysine

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of consideration variation and modification without departure from the scope of the appended claims.

What is claimed is:

1. A method of alleviating the deleterious effects of aging in a diabetic patient in need thereof, said effects being due to the production of 3DG by the enzymatic conversion of fructose-lysine (FL) to fructose-lysine-3-phosphate (FL3P), said method consisting of administering to said patient as the sole therapeutic agent an effective amount of an inhibitor of said enzymatic conversion of FL to FL3P, said inhibitor being a compound selected from the group consisting of sorbitollysine, mannitollysine, galactitollysine, 3-O-methyl sorbitollysine, meglumine and the pharmaceutically acceptable salts thereof.

2. The method of claim 1, wherein said inhibitor is meglumine or a pharmaceutically acceptable salt thereof.

3. The method of claim 1, wherein said inhibitor is administered in solid form, also comprising a pharmaceutically acceptable excipient.

4. The method of claim 1, wherein said inhibitor is administered in liquid form, also comprising a pharmaceutically acceptable diluent.

5. The method of claim 1, wherein said inhibitor is administered at a dosage level of about 0.7µg to about 20 mg of said inhibitor per kilogram of patient body weight per day.

6. The method of claim 5, wherein said dosage level is from about 30 µg to about 3.5 mg of said inhibitor per kilogram of patient body weight per day.

7. The method of claim 1, wherein said inhibitor is administered via a route selected from the group of oral, parenteral, intraperitoneal, or intravenous administration.

* * * * *